United States Patent [19]
Peterson et al.

[11] Patent Number: 5,520,639
[45] Date of Patent: *May 28, 1996

[54] NEEDLELESS HYPODERMIC INJECTION METHODS AND DEVICE

[75] Inventors: Steven F. Peterson, West Linn, Oreg.; Charles N. McKinnon, Jr., Laguna Niguel, Calif.; Paul E. Smith, Tualatin, Oreg.; Takaaki Nakagawa; Victor L. Bartholomew, both of Tigard, Oreg.

[73] Assignee: Bioject, Inc., Portland, Oreg.

[21] Appl. No.: 407,867

[22] Filed: Mar. 21, 1995

[*] Notice: The term of this patent shall not extend beyond the expiration date of Pat. No. 5,383,851.

Related U.S. Application Data

[63] Continuation of Ser. No. 97,266, Jul. 23, 1993, Pat. No. 5,399,163, which is a continuation-in-part of Ser. No. 920,106, Jul. 24, 1992, Pat. No. 5,383,851.

[51] Int. Cl.$^6$ ................................................. A61M 5/30
[52] U.S. Cl. ........................ 604/68; 604/72; 604/187; 604/140
[58] Field of Search ......................... 604/68–72, 147, 604/140–143, 187, 228, 232; 222/389

[56] References Cited

U.S. PATENT DOCUMENTS

| 2,380,534 | 7/1945 | Lockhart . |
| 2,670,121 | 2/1954 | Scherer et al. . |
| 2,704,543 | 3/1955 | Scherer . |
| 3,424,154 | 1/1969 | Kinsley . |
| 3,561,443 | 2/1971 | Banker . |
| 3,945,379 | 3/1976 | Pritz et al. . |
| 4,059,107 | 11/1977 | Iriguchi et al. . |
| 4,623,332 | 11/1986 | Lindmayer et al. . |
| 4,680,027 | 7/1987 | Parsons et al. . |
| 4,722,728 | 2/1988 | Dixon . |
| 4,790,824 | 12/1988 | Morrow et al. . |
| 4,850,967 | 7/1989 | Cosmai . |
| 4,913,699 | 4/1990 | Parsons . |
| 4,940,460 | 7/1990 | Casey et al. . |
| 4,941,880 | 7/1990 | Burns . |
| 5,009,637 | 4/1991 | Newman et al. . |
| 5,024,656 | 6/1991 | Gasaway et al. . |
| 5,062,830 | 11/1991 | Dunlap . |
| 5,064,413 | 11/1991 | McKinnon, Jr. et al. . |
| 5,073,165 | 12/1991 | Edwards . |
| 5,116,313 | 5/1992 | McGregor . |
| 5,383,851 | 1/1995 | McKinnon, Jr. et al. . |

Primary Examiner—C. Fred Rosenbaum
Assistant Examiner—Perry E. Van Over
Attorney, Agent, or Firm—Lyon & Lyon

[57] ABSTRACT

A needleless injection device includes an initiator valve controlling flow of compressed gas into a reservoir. A poppet valve connecting to the reservoir has a gas pressure regulation end to regulate flow from the initiator valve into the reservoir. A clamp piston is driven forward by gas pressure from the reservoir and causes jaws to clamp onto a plunger extending into an ampule. The poppet valve opens when reservoir pressure reaches the cracking pressure of the poppet valve. Gas from the reservoir rushes through the poppet valve into a drive chamber and forces a drive piston, containing the clamp piston and jaws, forward causing the plunger to slide into the ampule. A jet of injectant is discharged from the nozzle of the ampule and penetrates through the patient's skin. An improved method of needleless injection uses a specific pressure profile, ampule nozzle diameter, patient, injection site, and injectant parameters.

9 Claims, 29 Drawing Sheets

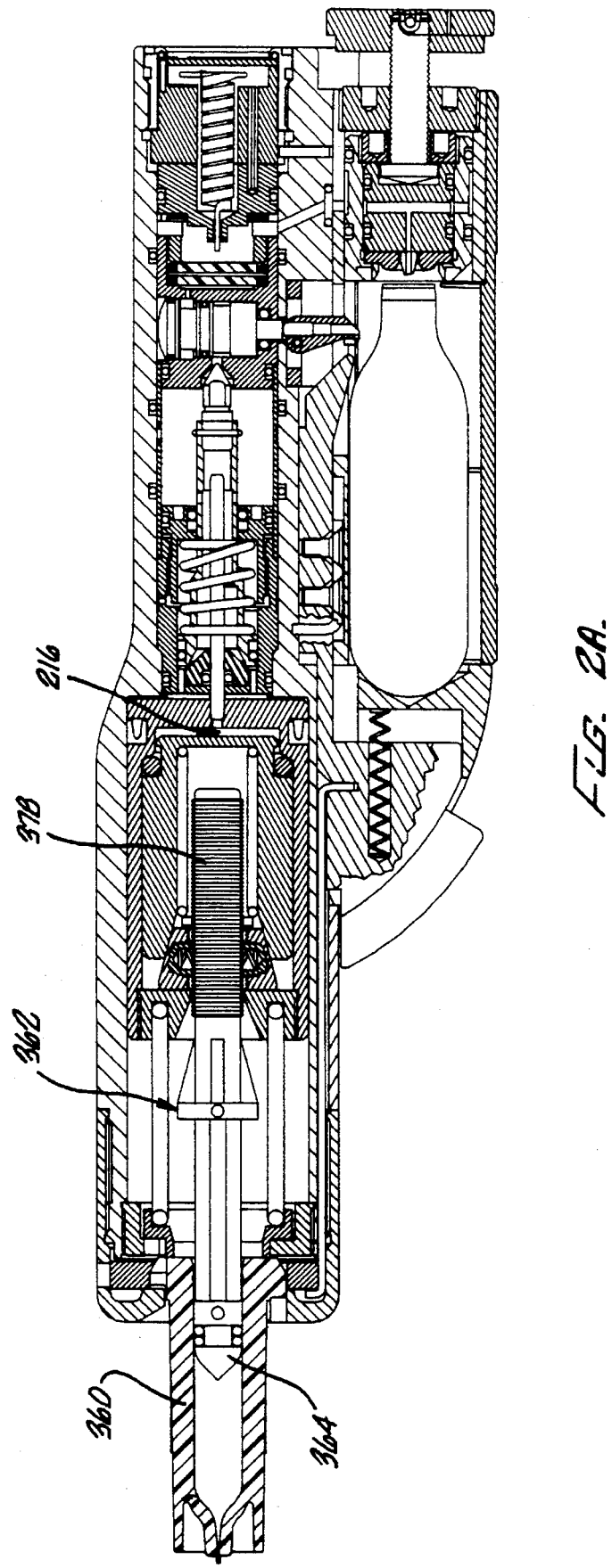

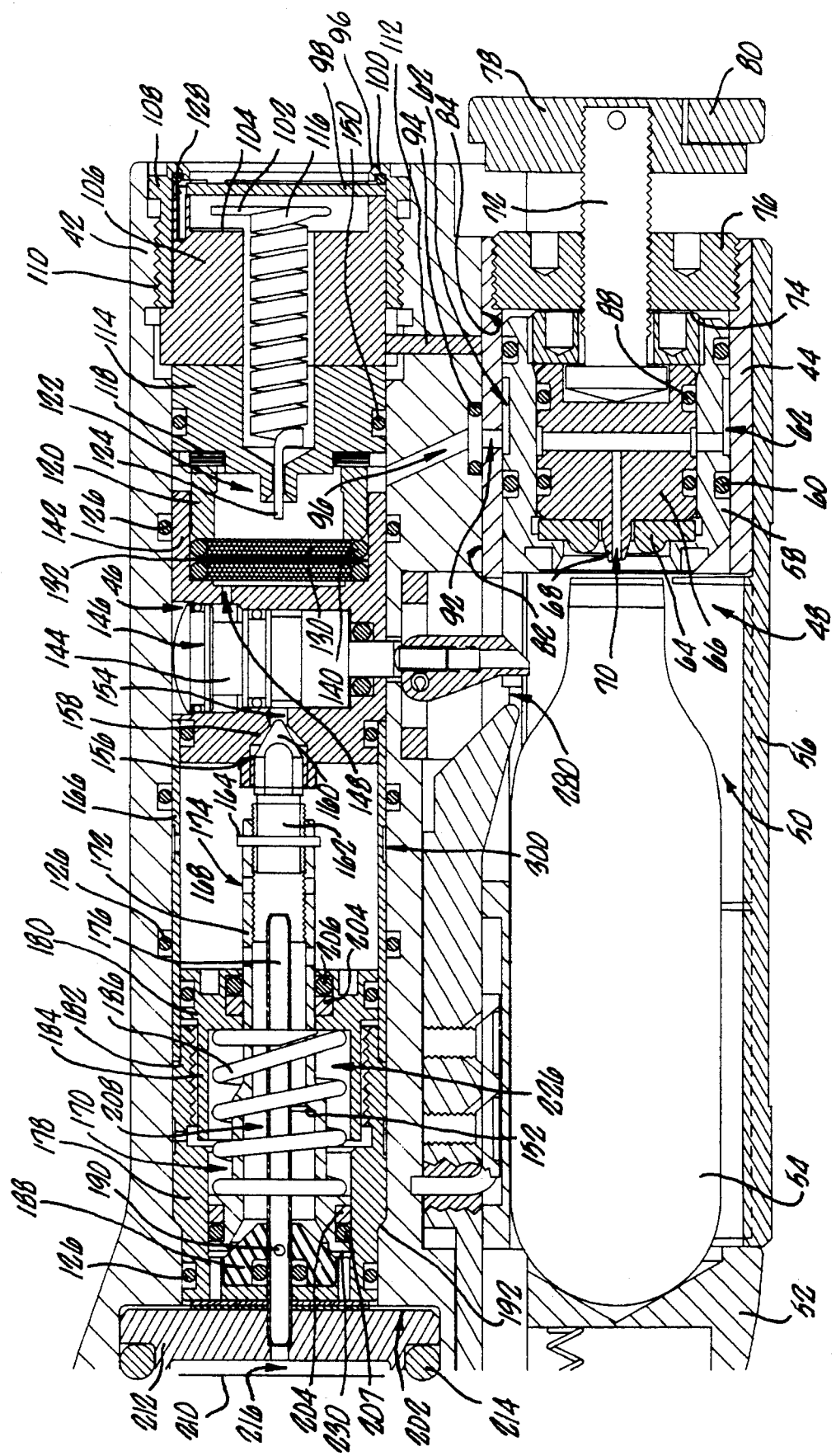

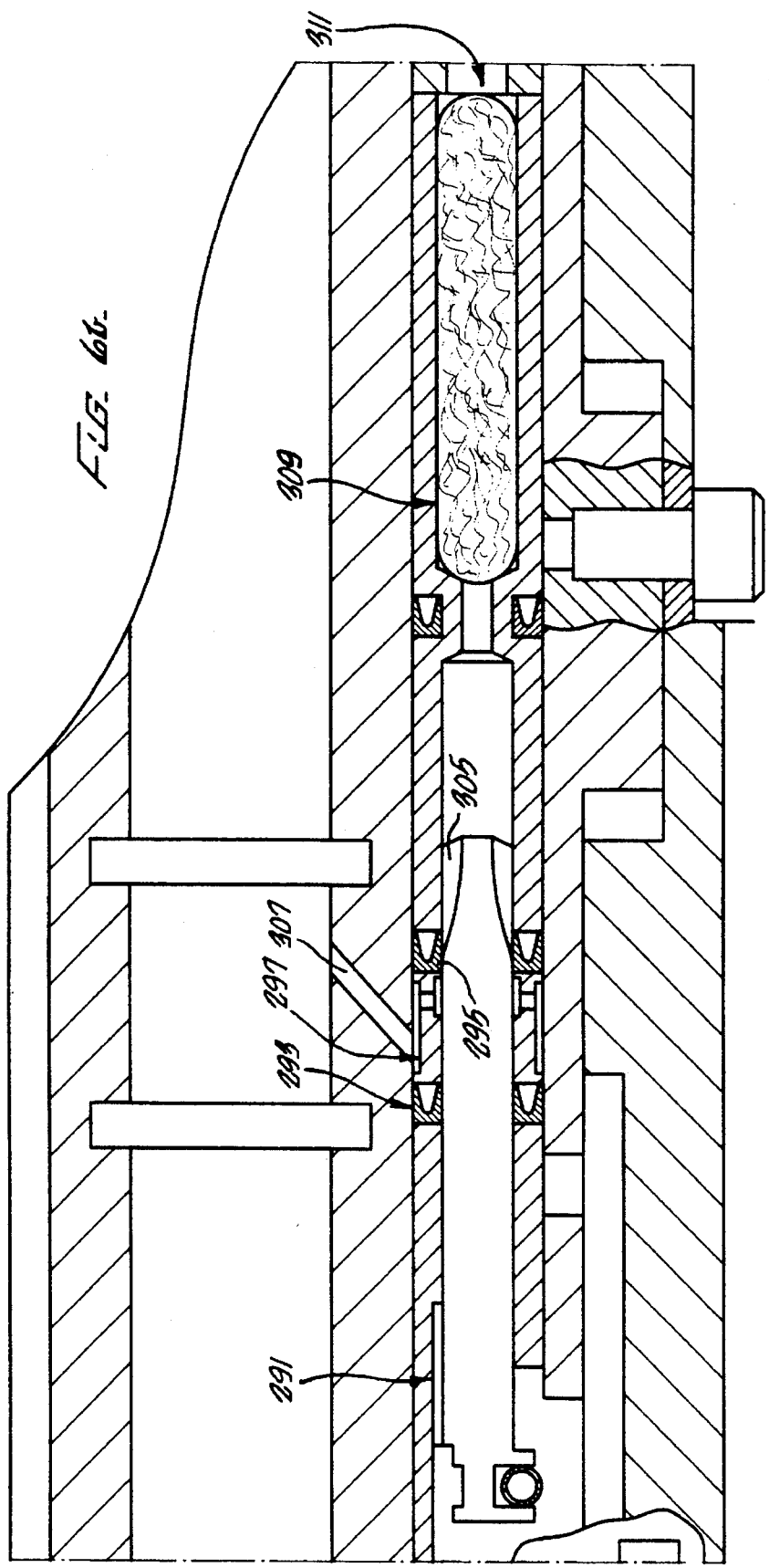

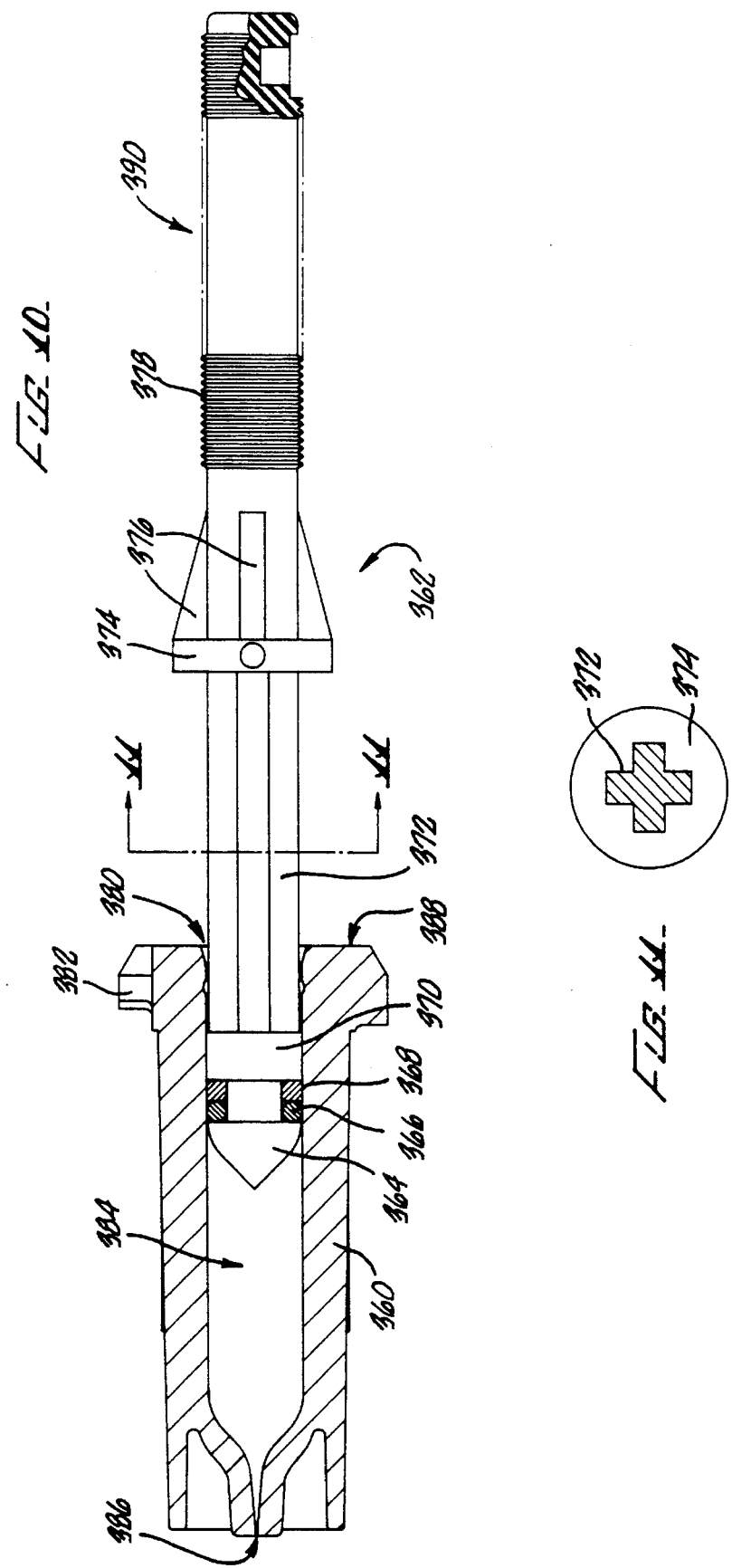

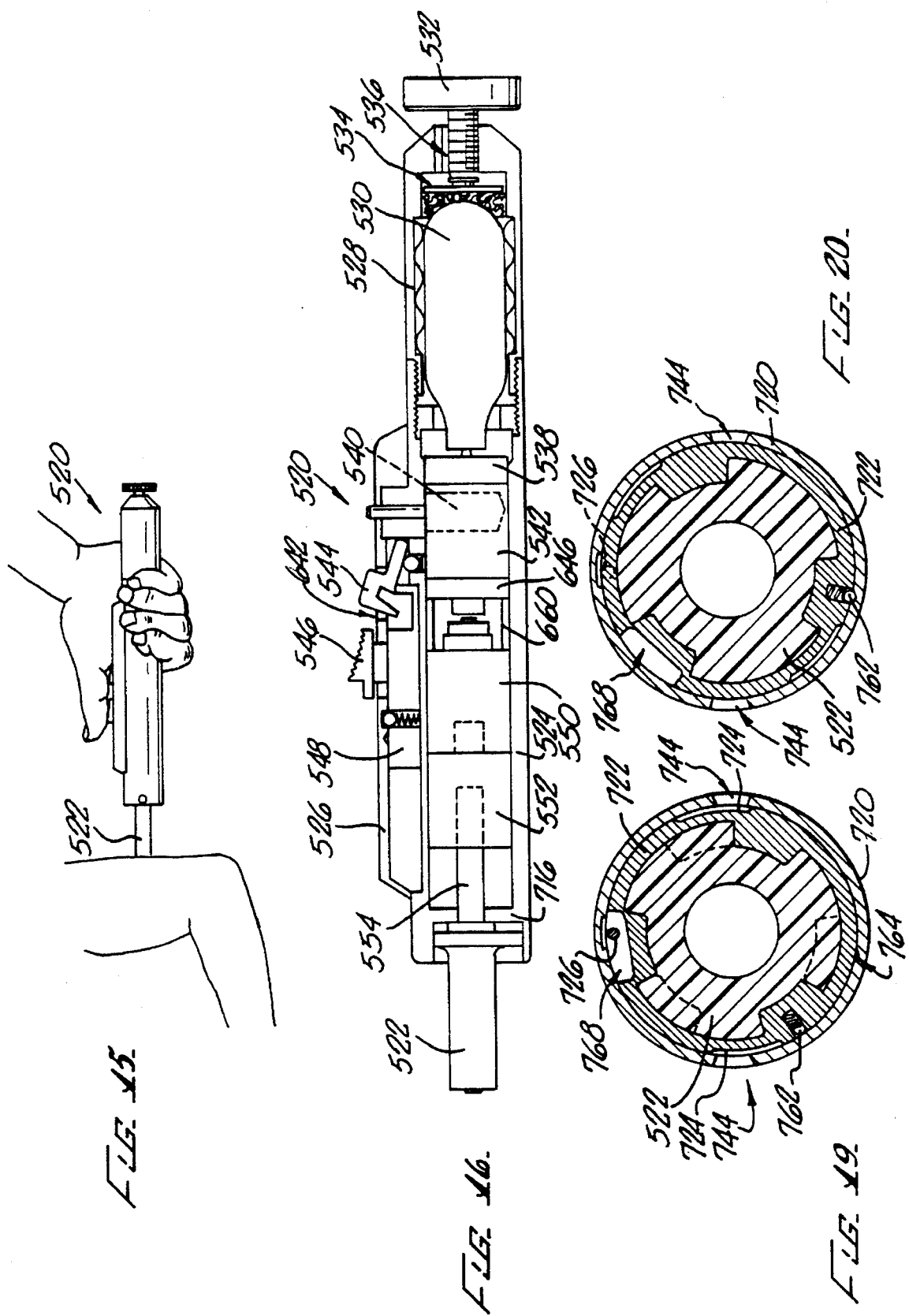

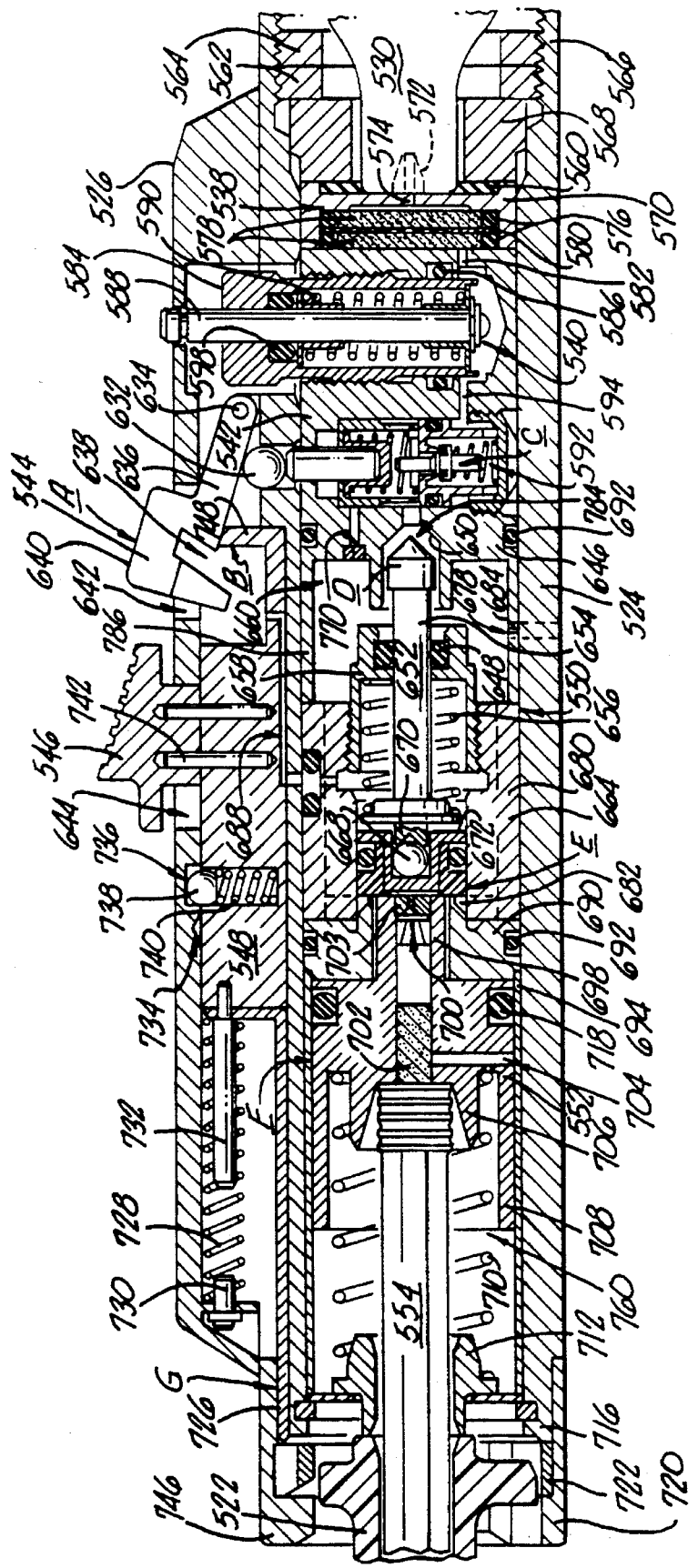

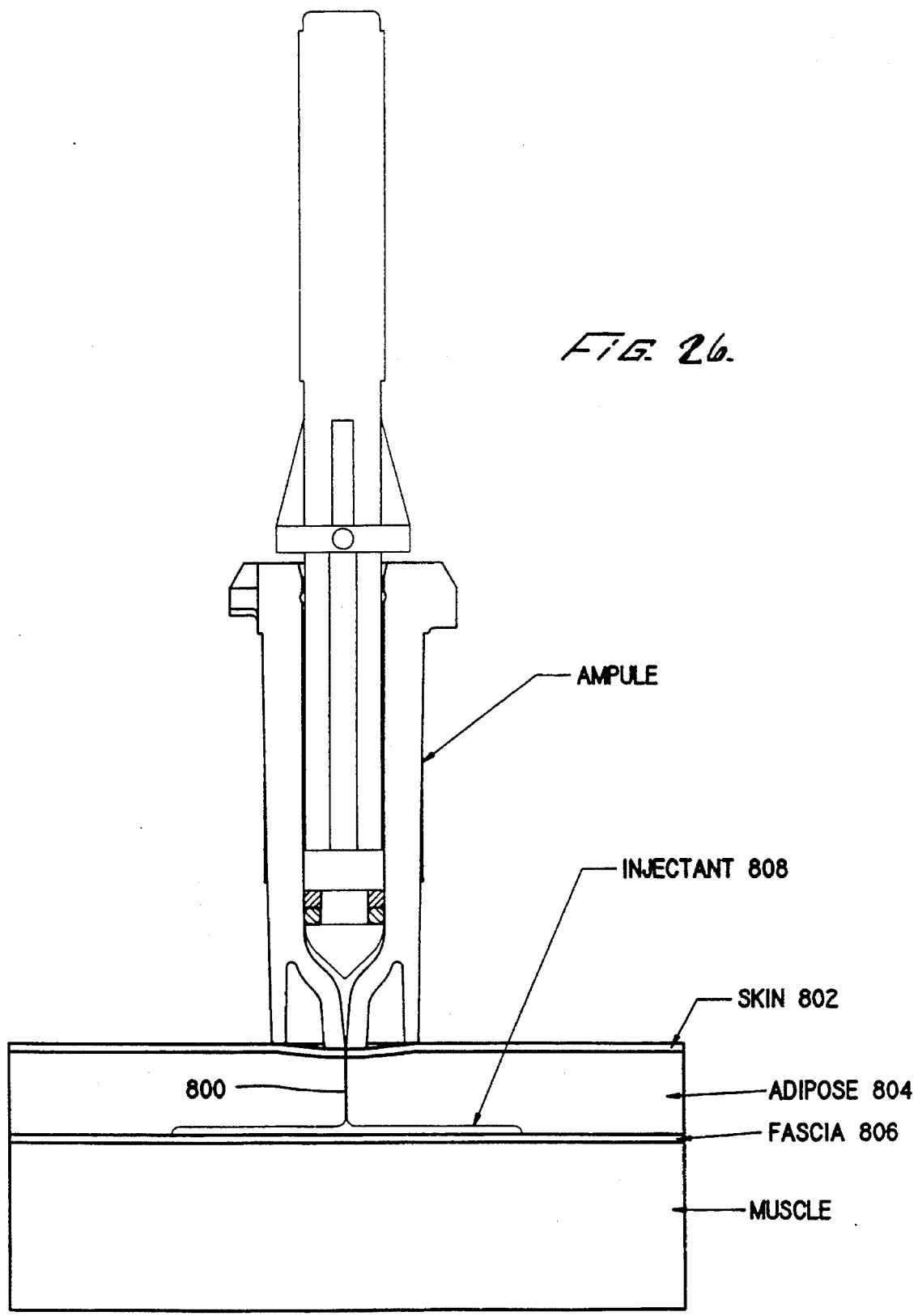

| APPLICATION | INJECTION SITE | PATIENT BODY TYPE | NOZZLE DIAMETER (INCHES) |
|---|---|---|---|
| FOR SUBCUTANEOUS INJECTIONS TO ALL PATIENTS USING STANDARD INJECTION SITES (i.e. LATERAL TRICEPS REGION, ABDOMEN, THIGH). | ALL STANDARD SC SITES | ALL PATIENTS | 0.004 |
| FOR IM INJECTIONS IN THE *THIGH* FOR SMALL INFANTS UP TO 15 LBS. ALSO FOR IM INJECTIONS IN THE *DELTOID* FOR THIN CHILDREN (21" TO 47" TALL AND WEIGHING 16 TO 50 LBS.). | THIGH DELTOID | 15" - 20" / 0 - 15 LBS. 21" - 47" / 16 - 50 LBS. | 0.006 |
| FOR IM INJECTIONS IN THE *THIGH* FOR INFANTS AND CHILDREN OF THIN TO AVERAGE HEIGHT AND WEIGHT (i.e. 21" TO 47" AND 16 TO 75 LBS.). ALSO USED FOR IM INJECTIONS IN THE *DELTOID* TO AVERAGE CHILDREN (i.e. OVER 50 LBS.) AND TO ADOLESCENTS AND ADULTS WHO ARE *LESS THAN* 80% OF LEAN BODY WEIGHT FOR THEIR HEIGHT. | THIGH OR GLUTEUS DELTOID | 21" - 47" / 16 - 75 LBS. CHILDREN OVER 50 LBS. ADULTS OF SMALL SIZE (i.e. WITH LESS THAN 80% OF LEAN BODY WEIGHT OF A GIVEN HEIGHT). | 0.008 |
| FOR IM INJECTIONS IN THE DELTOID TO ADOLESCENTS AND ADULTS WHO ARE *WITHIN* 20% OF LEAN BODY WEIGHT FOR THEIR HEIGHT. | DELTOID | ADULTS OF AVERAGE BODY SIZE (i.e. WITHIN 20% OF LEAN BODY WEIGHT FOR A GIVEN HEIGHT). | 0.010 |
| FOR IM INJECTIONS IN THE DELTOID TO ADOLESCENTS AND ADULTS WHO ARE *MORE THAN* 120% OF LEAN BODY WEIGHT FOR THEIR WEIGHT. | DELTOID | ADULTS OF LARGE BODY SIZE (i.e. WITH MORE THAN 120% OF LEAN BODY WEIGHT FOR A GIVEN HEIGHT). | 0.014 |

FIG. 21.

NEEDLELESS HYPODERMIC INJECTION METHODS AND DEVICE

BACKGROUND OF THE INVENTION

This is a continuation of Ser. No. 08/097,266 filed on Jul. 23, 1993, now U.S. Pat. No. 5,399,163 which was a continuation-in-part of Ser. No. 07/920,106, filed Jul. 24, 1992 now U.S. Pat. No. 5,383,851, and which is incorporated herein by reference.

The field of the present invention is needleless hypodermic injection methods and devices.

Various needleless hypodermic injection devices have been known and used in the past. These devices, also known as jet injectors, typically use spring or compressed gas driven plungers to accelerate an injectant to a velocity sufficient to pierce through the skin and enter the underlying tissues.

While large jet injection apparatus have been successfully used for mass inoculations, e.g. in the military services, these apparatus are relatively complex, costly, limited in performance and are not portable. Thus, injections using needles remain as the standard despite their disadvantages (for example, accidental needle sticks and risk of spreading infection to both the patient and medical professional; safe disposal of the used needle, patient's fear of needles; and pain caused by needle injections). Jet injection avoids or diminishes these disadvantages.

Although many portable needleless injectors have been proposed, these known devices have not achieved widespread acceptance in the medical field, due to a variety of factors.

Significantly, the characteristics of needleless or jet injections typically vary with the pressures exerted by the injection device, the nozzle diameter of the ampule, the patient's size, age and weight, the nature of the injection site, and the viscosity of the injectant.

The soft layers of tissue at standard injection sites in humans, listed in the order from outside to the inside are: 1) the dermis, 2) the adipose, 3) the deep fascia, a tough membrane that surrounds the muscle, and 4) the muscle. The deep fascia and the skin are the toughest layers to penetrate with a jet injection. The adipose tissue is the most easily penetrated.

Parenteral injections into humans are classified according to four well established tissue regions in which the injectant may be deposited. These are: intra-dermal, subcutaneous, intra-muscular, and intravenous. With intra-dermal injections, the injectant is deposited in the dermis layer. With subcutaneous (SC) injections, the injectant is deposited in the adipose tissue. With intramuscular injections (IM), the injectant is deposited in the muscle. Intra-venous are those injections deposited directly into a vein, an injection method generally not suitable for jet injection.

Intradermal injections, the least invasive of the three types, are employed when the dose is very small and it is desired to visualize patient response. Subcutaneous injections are employed when it is desired to prolong the time for absorption of the medication, when the dose is relatively small, or the injectant is non-irritating. Intramuscular injections, the most invasive of the three types, are employed when it is desired to have rapid absorption, when the medication is irritating, or when the dose is relatively large.

Absorption is not solely dependent on placement of the injectant, it is also dependent on the medication. Some medications are formulated to slow the rate of absorption. For example, intramuscular medications are sometimes oil based for this purpose. Similarly, subcutaneous medications sometimes contain crystalline compounds to delay absorption.

A long standing basic difficulty with jet injection has been the complex problem of determining which are the preferred injection variables. These variables include: 1) pressure profile, 2) nozzle size, 3) patient factors, i.e., age, sex and size, 4) injection site, and 5) medication viscosity. The repeated failures of the prior art to adequately solve these complex variables problems has contributed to the lack of acceptance of a handheld and portable jet injector in the medical community.

The pressure profile is the pressure exerted on the liquid injectant, typically measured over time, from the beginning to the end of the injection. The pressure profile must be selected, in combination with the nozzle size and other factors, to deliver the injectant through the skin to the desired depth, preferably with minimum pain.

The patient factors are also important. Gender is significant as women typically have a different adipose distribution than men. Men also typically have tougher tissue that women. The patient's age is important because infants are born with very little muscle, thick layers of adipose, and very easily penetrated skin. As infants age and become mobile the adipose is gradually replaced by muscle. At adolescence the introduction of hormones changes tissue composition. Aging through mid-life is usually associated with gradual weight gain and decrease in tissue strength.

Injection sites are very significant because in all patients the thickness of the skin and adipose tissue varies at different regions of the body. The medical profession has established generally accepted injection sites for conventional needle syringes that are best suited for specific types of injection. The subcutaneous sites typically have a thick adipose layer and are free of major nerves and vasculature. Intramuscular sites typically have a thin adipose layer, a thick muscle layer, and are free of major nerves and vasculature.

Finally, the viscosity of the injectant must be considered as it effects characteristics of the jet injection. In addition, it has been discovered that viscosity effects have been widely misunderstood in the prior art.

The prior art has generally not been able to overcome the complexities and difficulties of simultaneously accounting for all of the foregoing variables. Thus, jet injection, despite its great potential advantages, remains virtually unused. Accordingly, it is an object of the invention to provide improved methods and devices for needleless injection, so that the advantages of jet injection may be brought into use.

SUMMARY OF THE INVENTION

To these ends, in a needleless injection device, actuation of the device initially causes a valve to open. The device engages a plunger extending from an ampule. The plunger is then driven into the ampule generating a high velocity jet of injectant from the nozzle of the ampule. Variable doses of injectant can be provided as the device can engage any position of the plunger regardless of the plunger position.

Also, to this end, another needleless injection device has a trigger on a housing to actuate an initiator valve. A reservoir is filled with compressed gas by actuation of the trigger. Upon reaching a predetermined pressure, a second valve opens to allow compressed gas to flow and act on a piston to drive a plunger into an ampule. Simultaneously, the mechanical movement of the second valve closes off further gas flow into the reservoir.

An interlock system is advantageously provided to prevent the trigger from actuating the initiator valve unless an ampule is properly installed in the device. Preferably, filters prevent stray liquified compressed gas from entering into internal chambers of the device.

In novel methods of needleless injection, the pressure profiles of the injectant, nozzle diameter, patient and injection site parameters, as well as injectant viscosity, are selected to achieve desired injection characteristics.

The present invention also provides a method of perifascial injection wherein the injectant is purposely deposited on the deep fascia in a thin sheet. This provides rapid absorption into the blood stream, without the invasiveness, injection discomfort, and occasional post injection soreness associated with injection deep into the muscle.

BRIEF DESCRIPTION OF THE DRAWINGS

In the drawings, wherein similar reference characters denote similar elements throughout the several views:

FIG. 2a is a section view thereof further illustrating an ampule and plunger installed in the device with the device in a ready to inject position, except for the piercing mechanism, which is not shown having pierced the cartridge;

FIG. 3 is an enlarged view fragment of the section view of FIG. 2, generally showing the back half of the device;

FIG. 6a is a partial section view of a preferred alternative housing and piston plenum shut-off valve design;

FIG. 6b is a partial section view fragment of an alternative preferred exhaust valve used in the housing shown in FIG. 6a;

FIG. 6c is an enlarged partial section view of a bleed gas valve shown in FIG. 6a;

FIG. 7b is an enlarged section view fragment of an alternative preferred initiator valve;

FIG. 10 is a side elevation view in part section of the present plunger and an ampule;

FIG. 11 is a section view taken along line 11—11 of FIG. 10;

FIG. 15 is a perspective view of a second embodiment of the present needleless injection device in use to provide an injection into a patient's arm;

FIG. 17 is an enlarged section view fragment thereof showing the device of FIG. 15 prior to an injection;

FIG. 18 is a similar view thereof showing the device of FIG. 15 just after an injection;

FIG. 19 is a section view taken along line 19—19 of FIG. 18 and showing the interlock system of the device in the ready or unlocked position;

FIG. 20 is a similar section view of FIG. 17 showing the interlock system of the device of FIG. 15 in the locked position;

FIG. 26 is a schematic illustration of the present perifascial needleless injection;

FIG. 27 is a table showing ampule selection and parameters; and

DETAILED DESCRIPTION OF THE PREFERRED EMBODIMENTS

Figure 1:
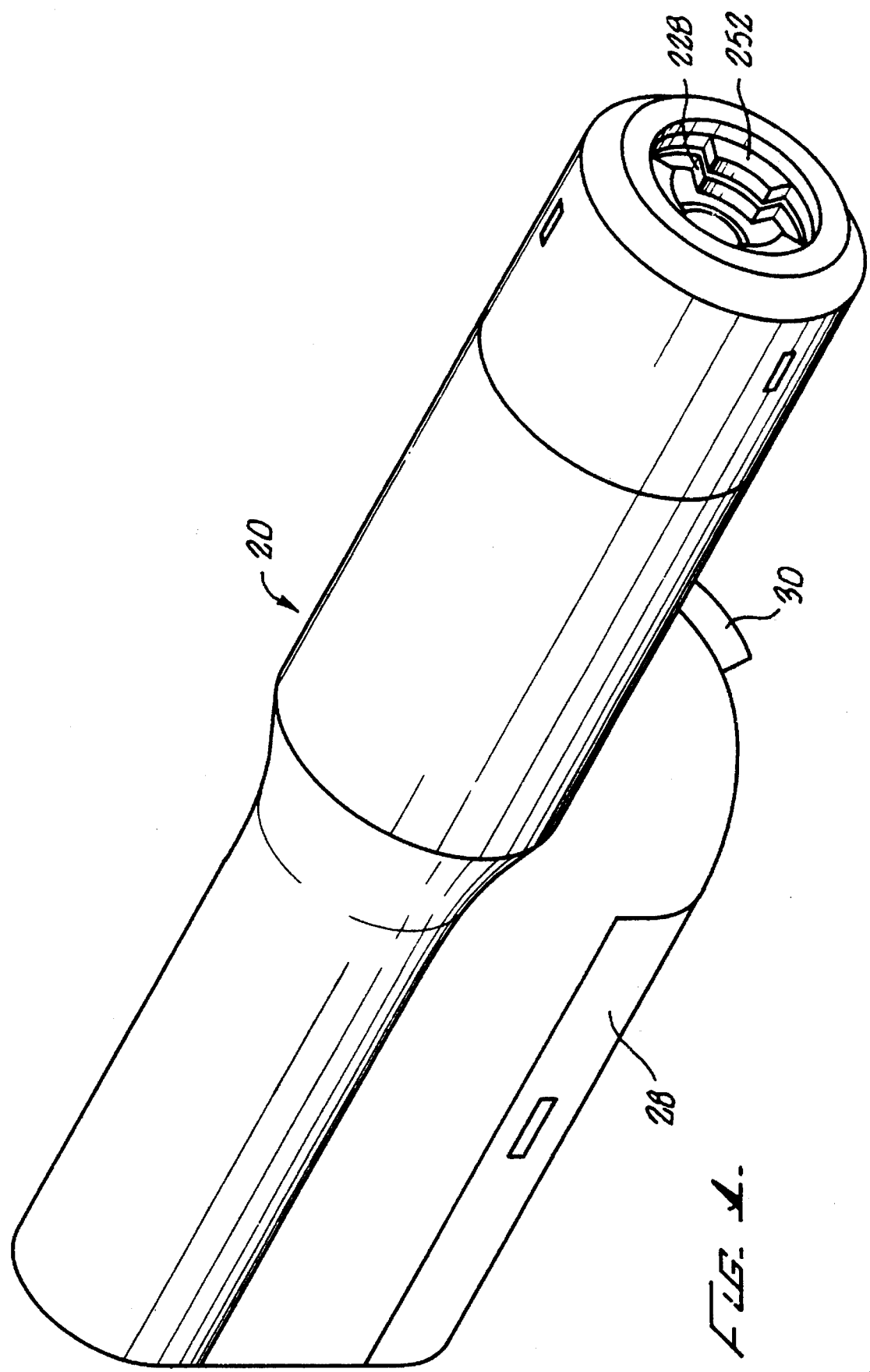
FIG. 1 is a perspective view of the present needleless injection device.
Figure 2:
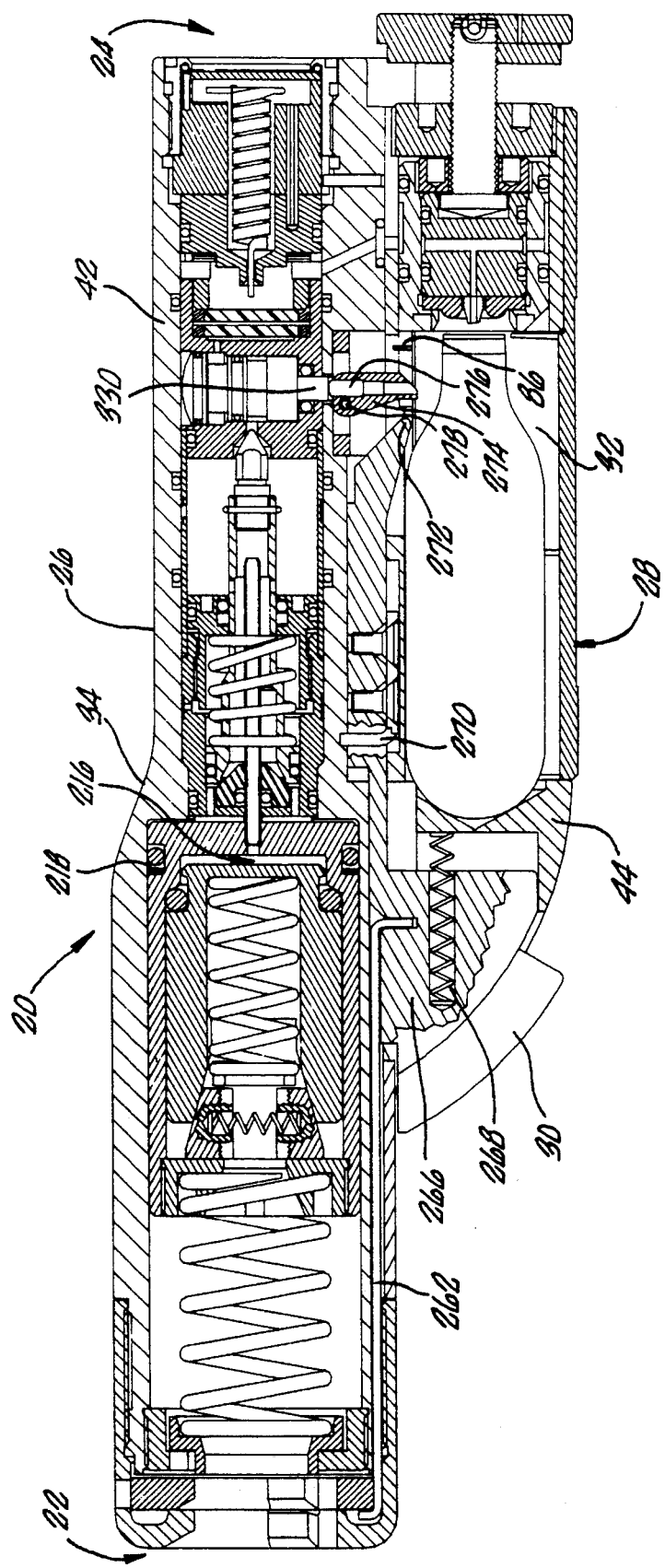
FIG. 2 is a section view of the present needleless injection device taken along line 2—2 of FIG. 8.

Turning now in detail to the drawings, as shown in FIGS. 1 and 2, an injector or needleless injection device 20 has a front end 22, a back end 24, a top surface 26 and a bottom surface 28. A trigger 30 is slidably mounted on the injector 20 adjacent the bottom surface 28. The injector 20 includes an upper housing 42 and a shorter lower housing 44 attached to the upper housing 42. The lower housing 44 has a flat upper surface 82 which lies against a flat lower surface 84 of the upper housing 42. The upper housing 42 and lower housing 44 are attached together with four (4) pins 86.

The upper housing 42 and lower housing 44 together are sized and shaped to readily fit the user's hand, with the user's palm resting over the top surface 26 and side of the injector 20, and with the user's index finger easily positionable over the trigger 30. The top surface 26 has a step or incline 34 at approximately the center of the injector 20. The upper and lower housings may alternatively be formed as a single housing.

Figure 6:
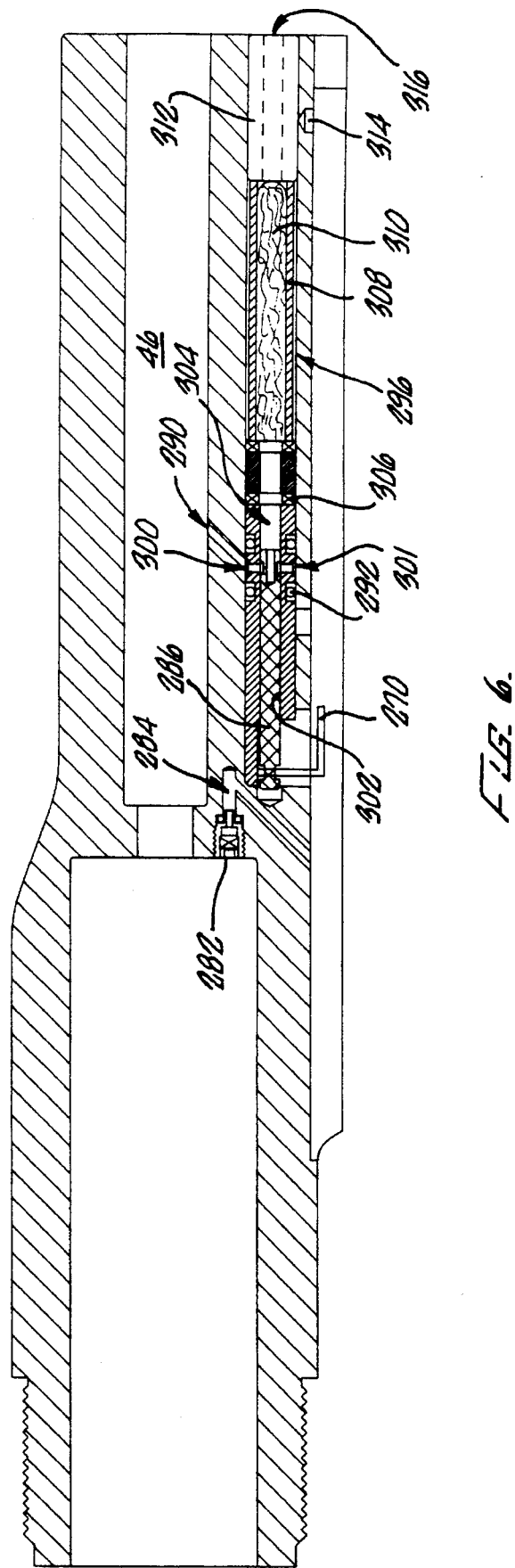
FIG. 6 is a partial section view fragment taken along line 6—6 of FIG. 8 and showing selected features only.
Figure 68:
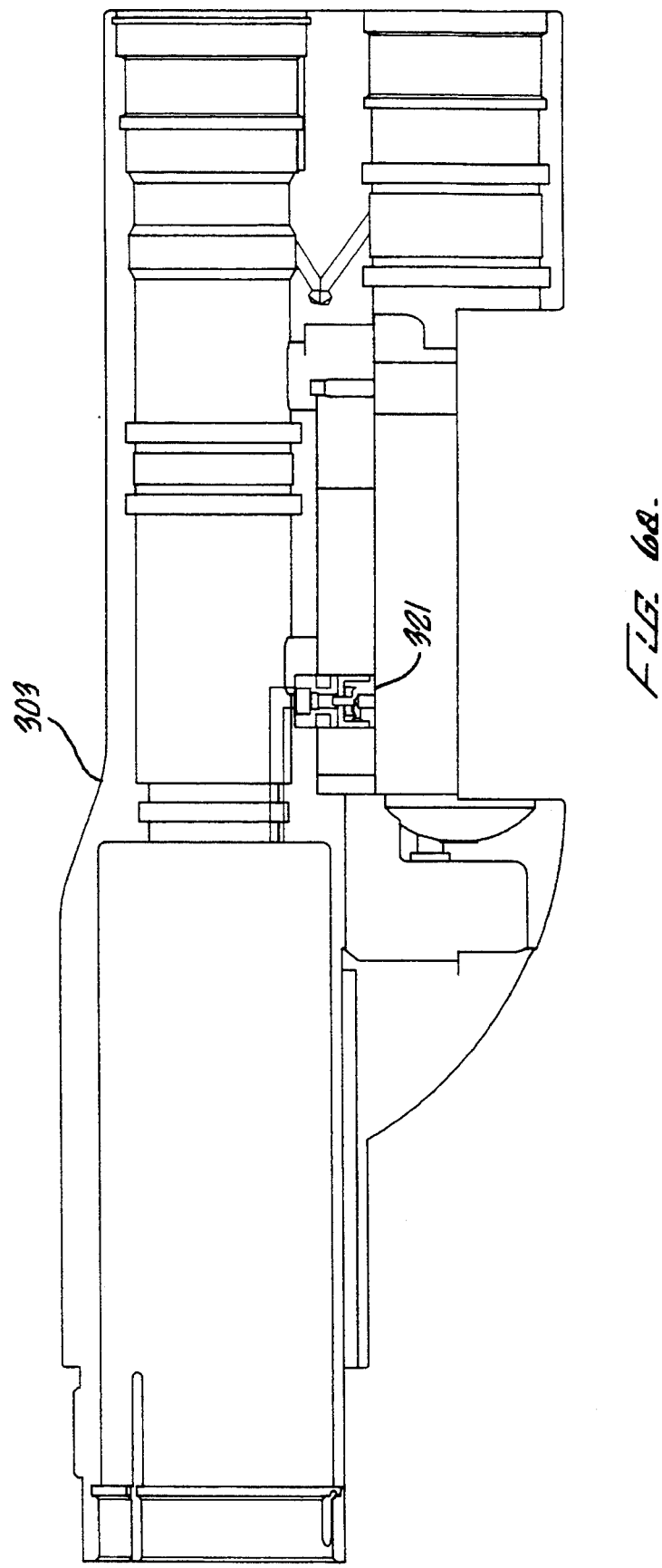

Turning to FIG. 3, the lower housing 44 is substantially hollow and defines a lower housing space 48. Similarly, the upper housing 42 defines an upper housing space 46 (FIG. 6). Within the lower housing 44 is a cartridge chamber 50 for receiving and holding a compressed gas cartridge 54, e.g., a $CO_2$ cartridge. A cartridge seat 52 at the forward end of the cartridge chamber 50 supports the back of the cartridge 54. A generally u-shaped plastic cartridge chamber cover 56 snaps into place on the lower housing 44 over the cartridge chamber 50.

A generally cylindrical piercing housing 58 is slidably positioned behind the cartridge chamber 50 within the lower housing 44. O-rings 60 seal the piercing housing 58 against the lower housing 44 while allowing the piercing housing 58 to slide within the lower housing 44. An annulus 62 extends around the circumference of the piercing housing 58 in between the o-rings 60. A cylindrical piercing body 66 is positioned within the piercing housing 58 and sealed against the piercing housing 58 by o-rings 88. A piercing point 68 extends forward from the front surface of the piercing body 66 and is centrally aligned with the neck of the cartridge 54. A seal 64 on the front end of the piercing body surrounds the piercing point 68. The seal 64 extends sufficiently forward to seal against the neck of the cartridge 54 before the piercing point 68 penetrates into the cartridge 54.

A bore 70 extends through the piercing point 68 and piercing body 66 connecting to the annulus 62. A piercing body nut 74 threads into the back end of the piercing housing 58, to secure the piercing body 66 and seal 64 in position within and against the forward end of the piercing housing 58. A piercing housing nut threads into the back of the lower housing 44. Spanner tool openings are provided in the piercing body nut 74 and the piercing housing nut 76 for assembly purposes.

A threaded shaft 72 extends through and engages threads in the piercing housing nut 76. A knob 78 attached to the threaded shaft 72 has a flip handle 80 which can be flipped up perpendicular to the plane of the knob 78 to allow the knob 78 and threaded shaft 72 to be more easily turned by hand. The forward end of the threaded shaft 72 bears against the back surface of the piercing body 66.

A hole 92 extends through the upper surface 82 of the lower housing to connect the annulus 62 to a bore 96 leading into the upper housing space 46. An o-ring 94 seals the connection of the hole 92 and bore 96.

Figure 8:
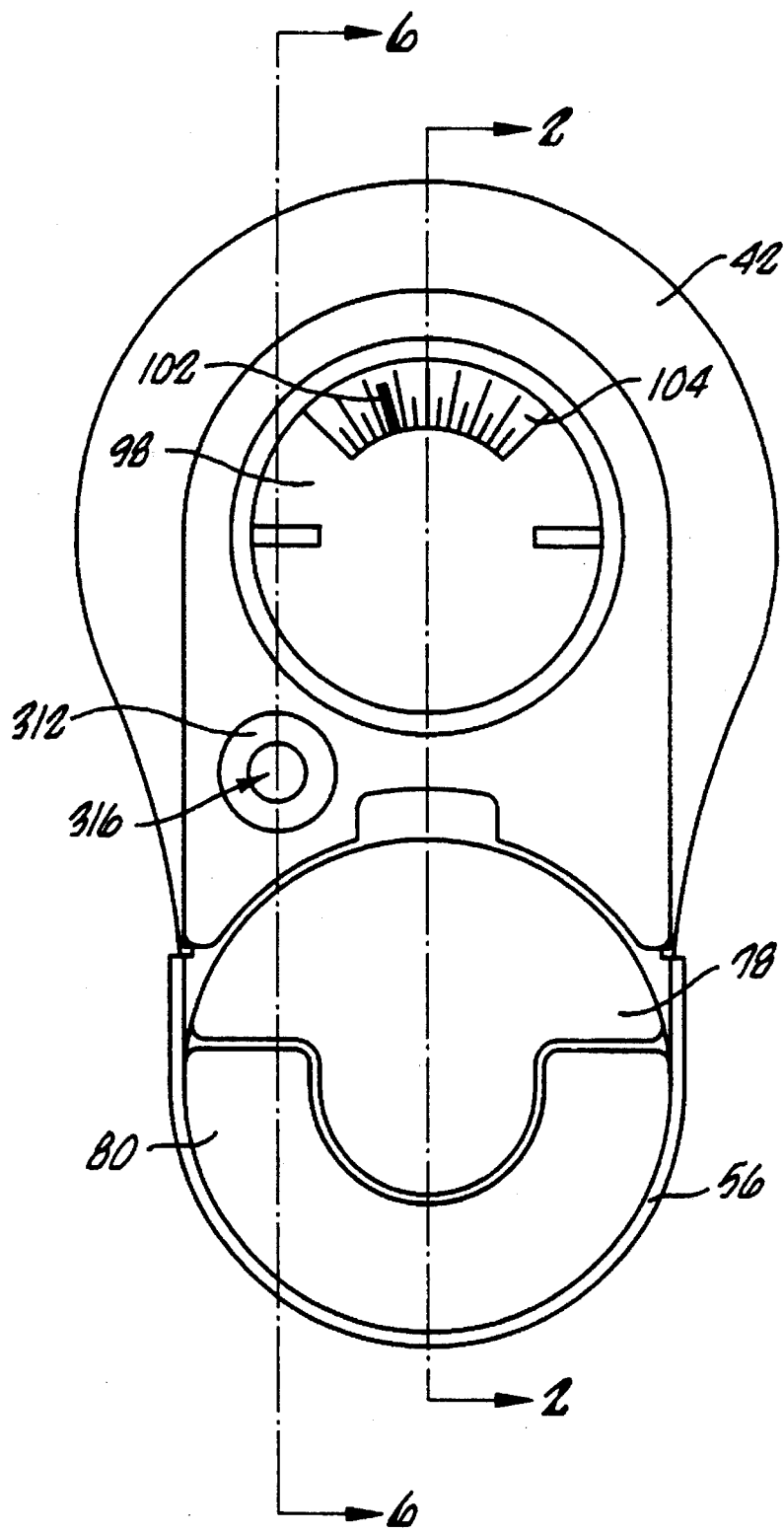
FIG. 8 is a back end elevation view of the device.

At the back end of the upper housing 42 is a transparent window lens 98 secured to an end nut 108 by a rubber window retainer 100. A Bourdon tube 116 is soldered into a gauge base 114 and has an open end 124 extending into a gauge chamber 122. The pointer 102 extends perpendicularly from the back end of the Bourdon tube 116. As shown in FIG. 8, a gauge label 104 applied to the back end of a gauge body 106 around the Bourdon tube 116 provides a calibrated pressure scale with the scale and pointer visible through the lens 98. Stop pins extending from the back end of the gauge body 106 provide high and low pressure end point stops for the pointer 102.

The end nut 108 has threads 110 at its forward end which engage the upper housing 42. To calibrate the gauge for a given pressure, the gauge body 106 is rotated relative to the gauge base 114. When the correct index is achieved, the gauge body 106 and gauge base 114 are adhered together. A guiding pin 112 extends from the upper housing 42 into a keyway groove and holds the gauge body 106 in place while the end nut 108 is tightened.

Shims 118 are provided at the front surface at the gauge base 114, as required, for proper stack up and positioning of components in the upper housing 42.

An initiator valve housing 142 is spaced apart from the gauge base 114 by a filter retainer ring 120. A sandwiched assembly of filter disks 130 and synthetic filters 132 are contained within the back end of the housing 142. The filter disks 130 are preferably sintered stainless steel or bronze (and preferably 2.0 micron, 0.062 inch×0.500 inch diameter available from NUMET). The synthetic filter 132 separating the two filter disks 130 is preferably three layers of Tyvek 1025D, 0.006 inch×0.625 inch diameter, available from DuPont. Tyvek is a DuPont trademark for a high density polyethylene spunbonded olefin fiber material. O-rings 140 seal the filter disks 130 against the retainer 140 and synthetic filter 132. O-ring 126 seals the filter retainer 140 within the upper housing 42. O-ring 126 and o-ring 150 seal the gauge chamber 122 such that compressed gas provided through the bore 96 can flow out of the gauge chamber 122 only through the filters.

A port 148 extends through the back wall of the initiator valve housing 142 into an initiator valve chamber 146 within the housing 142. An initiator valve 144 within the initiator valve chamber 146 controls gas flow from the port 148 through the initiator valve chamber 146 to a reservoir port 154 formed through the forward wall of the initiator valve housing 142.

A regulation valve 156 includes a regulation seat 158 formed around the reservoir port 154. A dart 160 moves into and out of the regulation seat 158. The dart 160 has a threaded dart shaft 162 threaded into the narrower tube section at the back end of a poppet body 172. A dart pin 164 extending through the tube section of the poppet body 172 and the threaded dart shaft 162 secures the adjustment of the longitudinal position of the dart 160 in relation to the regulation seat 158. A reservoir spacer 166 within the upper housing 42 extends from the forward end of the initiator valve housing 142 to a poppet housing 178, forming a reservoir 168 around the tube section of the poppet body 172. O-rings 126 seal the reservoir spacer 166 against the upper housing 42 and seal the initiator valve housing 142 to the reservoir spacer 166.

Figure 5:
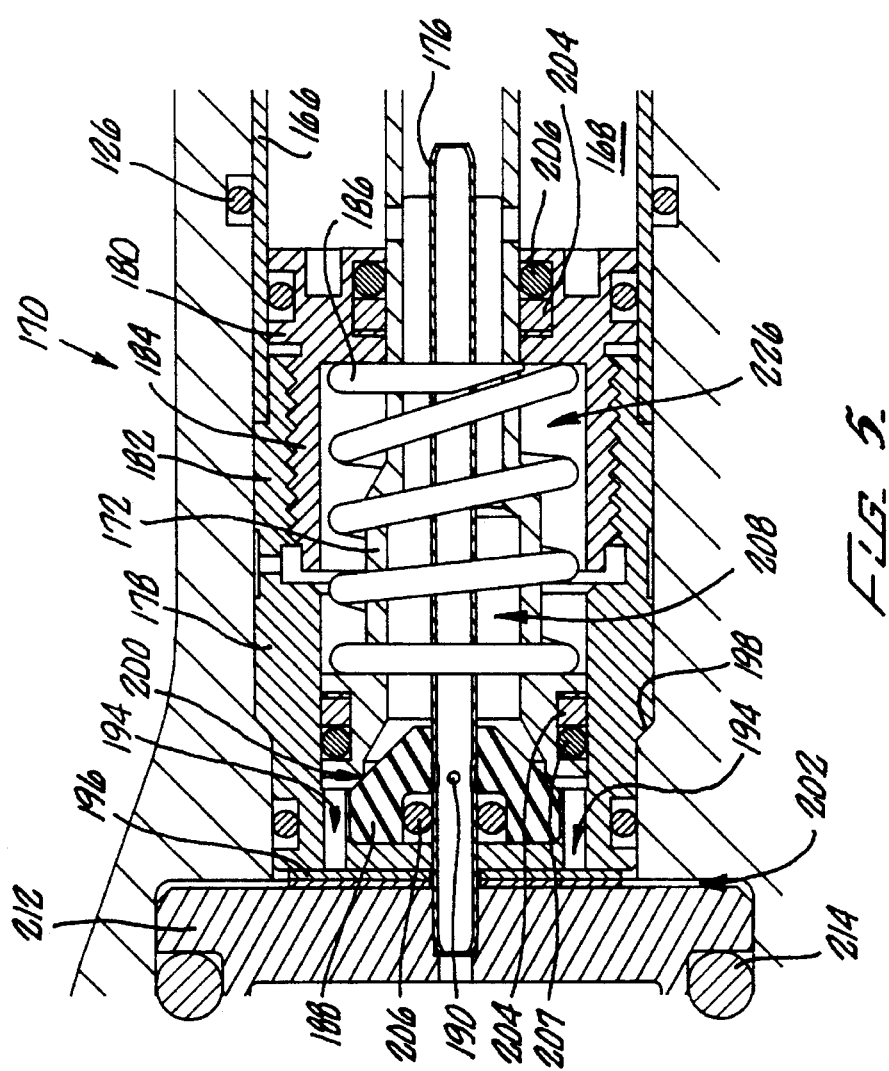
FIG. 5 is a further enlarged section view fragment of a valve shown in FIG. 3.

A poppet valve 170 within the poppet housing 178 has a conical plastic poppet seat 188 centered within and positioned against a forward wall of the poppet housing 178. Referring to FIG. 5, the poppet body 172 has a sharp sealing edge 200 biased against the poppet seat 188 by a compression spring 186 held in position within the poppet housing 178 by a poppet nut 180. Alternatively, the sealing edge 200 and poppet seat 188 may be configured with unlike angles selected so that the inner diameter contacts first, to minimize creep effects. The poppet nut 180 has a threaded forward section 184 engaged to a threaded rear section 182 of the poppet housing 178. The poppet nut 180 is turned to adjust the compression on the spring 186 and correspondingly set the cracking pressure of the poppet valve 170. Preferably, the poppet valve 170 is designed to crack open at 450 p.s.i.

The diameter of the poppet seat 188 exposed to reservoir pressure prior to crack (thus that which governs cracking pressure) remains constant although the conical seat may creep, as the sealing surface, facing reservoir pressure, is parallel to the axis of poppet movement. As the plastic creeps, stress on the plastic is reduced by increased contact area on the outer part of the conical seat. Yet, the sealing diameter remains unchanged. Thus, creep is self healing and some creep is allowed without sacrificing cracking pressure consistency.

The conical seat is attached to the poppet housing 178 rather than the poppet body 172 while all hard (poppet) parts are made concentric and perpendicular. Thus, irregularities in the seat 188 or soft part will creep to conform to hard parts. The hard parts are free to rotate but will still conform to the existing soft part deformation.

Sliding friction of the poppet body 172 is advantageously minimized and consistent. Hence, the seal 206 used with the back up ring 204 may be a low friction seal such as a rubber U-packing equivalent to a Parker 8400 series seal. In addition, since this seal is pressurized only after cracking due to the poppet body being pressurized internally before cracking, seal friction is greatly minimized. The poppet body begins to move during opening before this seal is pressurized. Thus, breakway friction is not increased by gas pressure. This minimizes time dependency of cracking pressure. Without this feature, it has been found that ampule peak pressure rises with time between shots.

By appropriate selection of the poppet sealing diameters (i.e., the tube section o.d., poppet housing i.d. and conical seal contact diameter) and spring force, i.e., for an approximately 450 p.s.i. cracking pressure and an approximately 150 p.s.i. regulation pressure, the poppet and regulation valves together can act as a low pressure regulator.

A cannula 176 is attached to and extends back from a drive piston 212 in front of the poppet valve 170 through the poppet housing 178 and poppet seat 188 and into the back section of the poppet body 172. Poppet body supply holes 174 extend through the poppet body 172 (FIG. 3). A cannula exhaust hole is provided through the cannula 176 at a position just slightly behind the o-ring 207 which slidably seals the cannula 176.

Referring still to FIG. 5, radially spaced apart drive bores 194 extend through the poppet housing 178 and connect a poppet annulus 198 to the front surface of the poppet housing 178. The poppet annulus 198, a ring-shaped space, is formed by the inside walls of the poppet housing 178, the front surface of the poppet 172 and the conical surface of the poppet seat 188. The front ends of the drive bores 194 are sealed by a preferably rubber disk drive bore seal 196 adhered to the back surface of the drive piston 212.

A joggle 192 in the poppet housing 178, which engages a corresponding lip within the upper housing 42, acts as a stop for the poppet housing 178. The reservoir spacer 166, initiator valve housing 142, filter ring, shims and the gauge body 106 are then subsequently installed within the upper housing 42 and stack up against the poppet housing 178, with the end nut 108 clamping these components in place.

The poppet nut can be rotated to adjust cracking pressure, after the injector is assembled. A window or opening, located in the compressed gas cartridge chamber, extends through the injector housing and through the poppet housing 178. The threaded forward section 184 of the poppet nut has spanner-like holes. A tool extending through the window can engage these holes to turn the poppet nut to adjust cracking pressure.

Still referring to FIG. 5, an o-ring 206, or more preferably a cup seal, slidably seals the poppet body 172 against the poppet housing 178 and poppet nut 180. The o-ring 206 and back up rings 204 prevent metal to metal contact during movement of the poppet body 172 and also act as pivots and guides to allow slight eccentricity between the poppet body 172 and poppet nut 180. Seal 207, preferably a cup seal, slidably seals to the poppet body or rod 172 to the poppet housing 178.

With the drive piston 212 at its rear most position (i.e., with the injector 20 in the "ready" condition), a ring-shaped plenum 202 is formed between the poppet housing 178 and the drive piston 212, or the o-ring 214 which slidably seals the drive piston 212 within the upper housing 42. The plenum 202 is just wide enough to insure compression on the face seal 195. During actuation, the entire back surface of the drive piston 212 is acted upon by compressed gas. A backup ring 218 is provided adjacent to the drive piston seal 214 which is preferably a low friction U-packing, equivalent to a Parker 8400 series seal.

Figure 4:
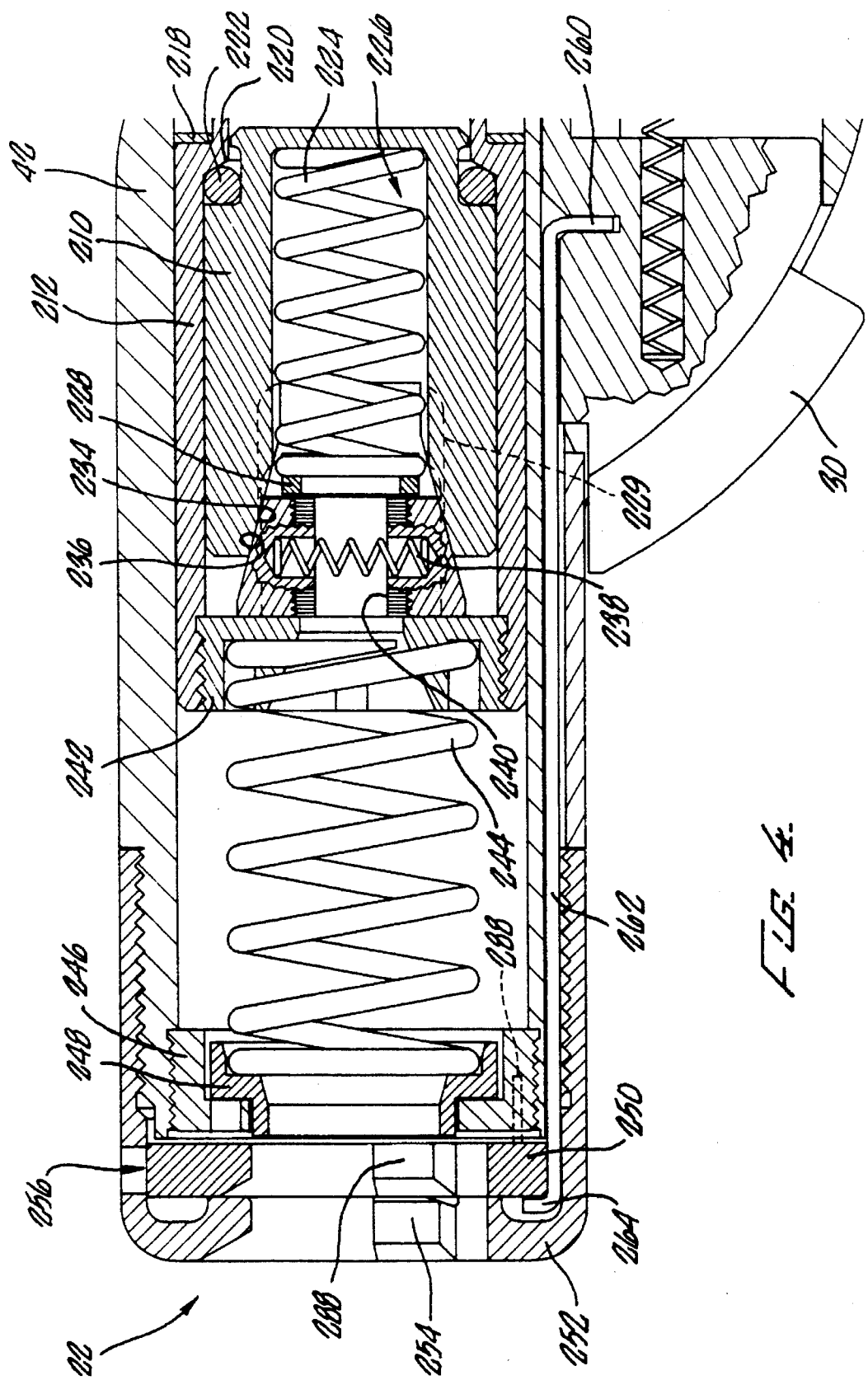
FIG. 4 is an enlarged view fragment of the section view of FIG. 2, generally showing the front half of the device.

Turning to FIG. 4, a clamp piston 210 is slidably positioned within the drive piston 212 and slidably seals against the drive piston 212 with a clamp piston o-ring 222. The back surface of the clamp piston 210 and the front vertical wall of the drive piston 212 form a clamp piston plenum 216 (FIG. 3).

An o-ring joggle 220 adjacent the back end of the drive piston 212 acts as a stop for the clamp piston o-ring 222. A clamp piston spring 224 within the clamp piston 210 biases forward a jaw plate 228 butting against two opposing flange walls 229 (shown in phantom in FIG. 4) extending from a jaw retainer nut 242, allowing just enough clearance for the jaws to move freely. The force of the clamp piston spring 224 is accordingly transferred from the plate 228 to the flange walls 229 to the jaw retainer nut 242 and bypasses the clamp jaws 236. The clamp jaws 236 are biased outwardly or apart and away from each other by a pair of spaced apart jaw springs 238. The clamp jaws 236 have teeth 240. Each clamp jaw 236 has a planar ramp surface 234 flatly engaged by a corresponding planar ramp drive surface 232 on the forward end of the clamp piston 210. The surfaces 234 and 232 are preferably inclined at about 15 degrees to horizontal. This angle is selected to provide a proper balance between friction losses, contact surface length, travel and clamping force. The jaw retainer nut 242 is threaded into the front end of the drive piston 212.

A return spring 244 is compressed in between the jaw retainer nut 242 and a pressure plate 248. A forward nut 246 threaded into the forward end of the upper housing 42 supports the pressure plate 248.

Figure 13A:
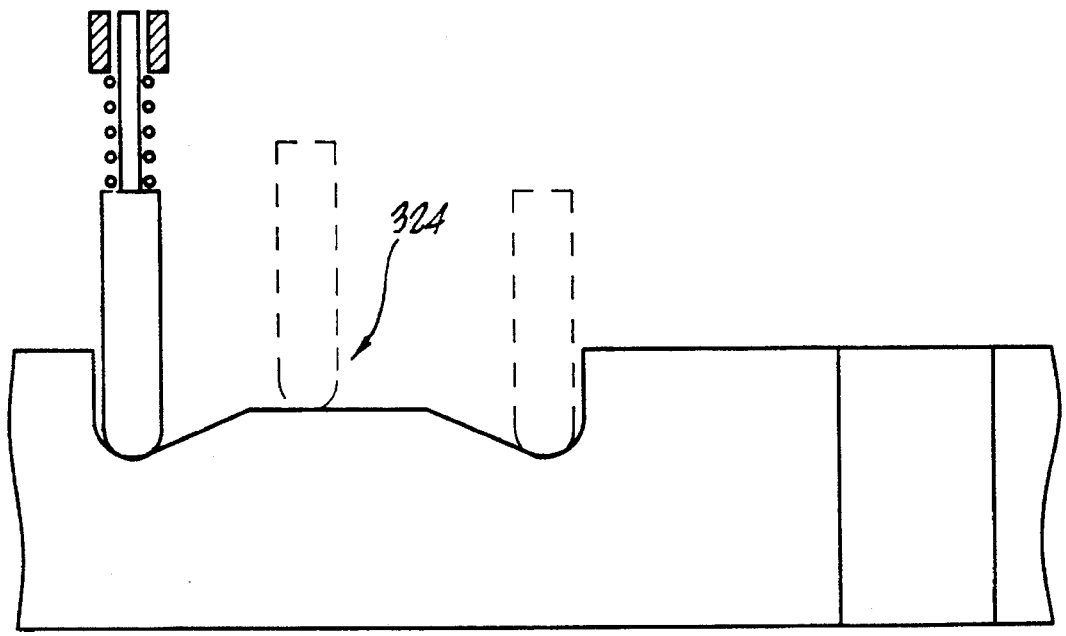
FIG. 13a is a side elevation view fragment taken along line 13a—13a of FIG. 13.
Figure 13:
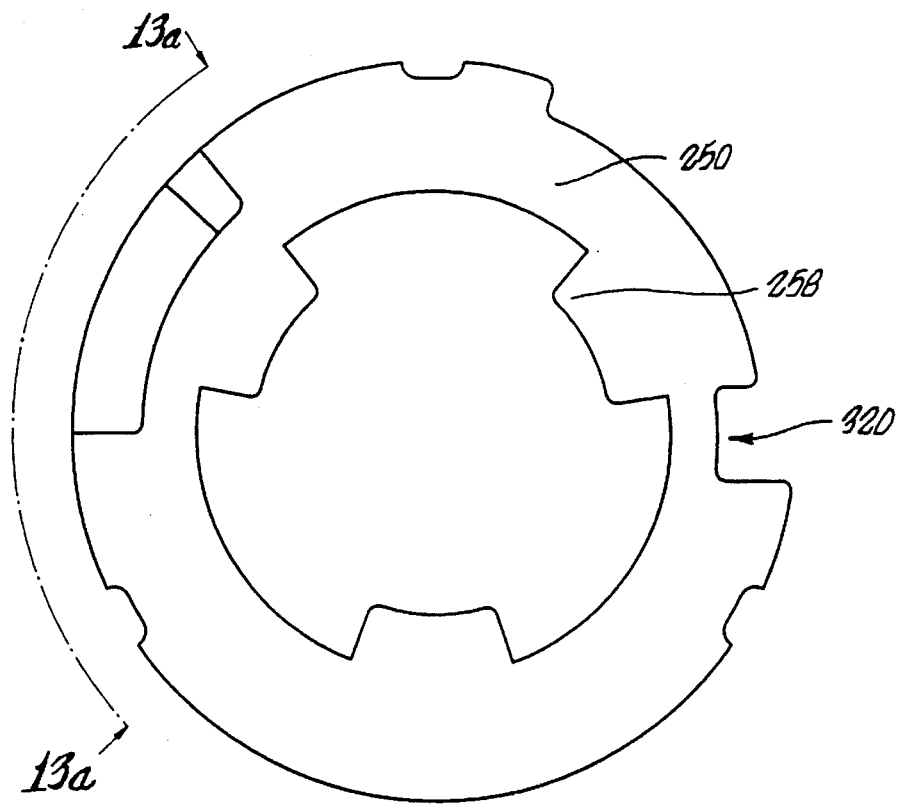
FIG. 13 is a front elevation view of the indicator ring shown in FIG. 4.
Figure 14:
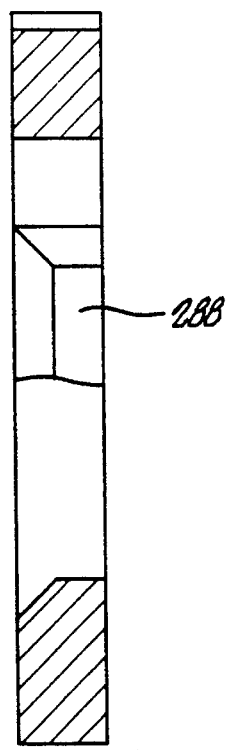
FIG. 14 is a side elevation view thereof in part section.

An indicator ring 250, as shown in FIGS. 13 and 14, is rotatably positioned in between the front end of the upper housing 42 and a front collar 252 threaded onto the front end of the upper housing 42. The indicator ring 250 has colored sections on its outside edge visible through view ports 256 in the front collar 252, when the indicator ring 250 is turned to a ready to actuate position signifying that the ampule lugs are fully engaged with the injector lugs. A detent pin 288 biased against the back surface of the indicator ring 250 holds the indicator ring in either the ampule loading/unloading position or the ready position, and provides a positive tactile (and optionally an audible click) indication that the ampule is correctly and fully installed. Referring to FIG. 13a, the detent pin 288 slides in or slides against a track 324 cut into the back of the indicator ring.

The return spring 244 biases the pressure plate 248 forward, to clamp an ampule behind the lugs 254 on the front collar 252, and it also acts to return the drive piston after an injection.

The indicator ring 250 has three equally spaced apart turning lugs 258 extending inwardly, for engaging the lugs 382 at the back of an ampule 360 (FIG. 10). The front collar 252 has three equally spaced apart retaining lugs 254 extending radially inwardly, for engaging the front surfaces of the ampule lugs 382, to hold the ampule into the injector 20.

Referring to FIGS. 2 and 4, an actuator link 262 has a forward hook 264 in front of the indicator ring 250. A rear hook 260 on the actuator link 262 is attached to an actuator slide block 266 slidably mounted in between the upper housing 42 and lower housing 44. A slide block spring 268 pushing off of the lower housing 44 forwardly biases the actuator slide block 266. The forward surface of the actuator slide block 266 forms the trigger 30.

Referring to FIGS. 2 and 6, an exhaust valve fork 270 extends laterally and upwardly from the actuator slide block 266 to engage a collar on a spool valve 286. The slide block 266 has a rounded back end 272 facing an initiator valve cam 274 pivotally attached to a holder with a roll pivot pin 278. Together they are held in a cavity in the upper housing by the upper surface of the lower housing. A gap 280 separates the rounded slide block end 272 and the initiator valve cam 274 (FIG. 3). A set screw 276 threaded into the initiator valve cam 274 engages an initiator pin in the initiator valve 144.

As shown in FIG. 6, an orifice 282 in the upper housing 42 connects to a drive plenum exhaust bore 284 to continuously vent or bleed the drive plenum 202 to ambient pressure. The orifice has an approximately 0.004 in. diameter opening. The spool valve 286 attached to the exhaust valve fork 270 is slidably positioned within a spool housing 294 secured within an exhaust passage 296 in the upper housing 42. The spool valve 286 fits within a spool bore 302 in the spool housing 294 with a very close tolerance. While the spool valve 286 does not absolutely seal against the spool bore 302, leakage between them is very low. No o-rings are used on the spool valve to reduce static and sliding friction.

A reservoir exhaust bore 290 links the reservoir 168 to a spool valve plenum 300 around the spool valve 286. A spool valve hole 301 leads from the spool valve plenum 300 to an exhaust duct 304 behind the spool valve 286. O-rings 292 are positioned on either side of the spool valve plenum 300 to seal the stationary spool valve housing 294 around the reservoir exhaust bore 290. Muffler seals 306 seal the forward end of the spool valve housing 294 against a muffler tube 308 filled with fiberglass wool 310 or other acoustic material and leading to an exhaust port 316 open to ambient pressure. A muffler retainer 312 and set screw 314 secure the spool valve housing 294, muffler seals 306 and muffler tube 308 within the exhaust passage 296.

Figure 7:
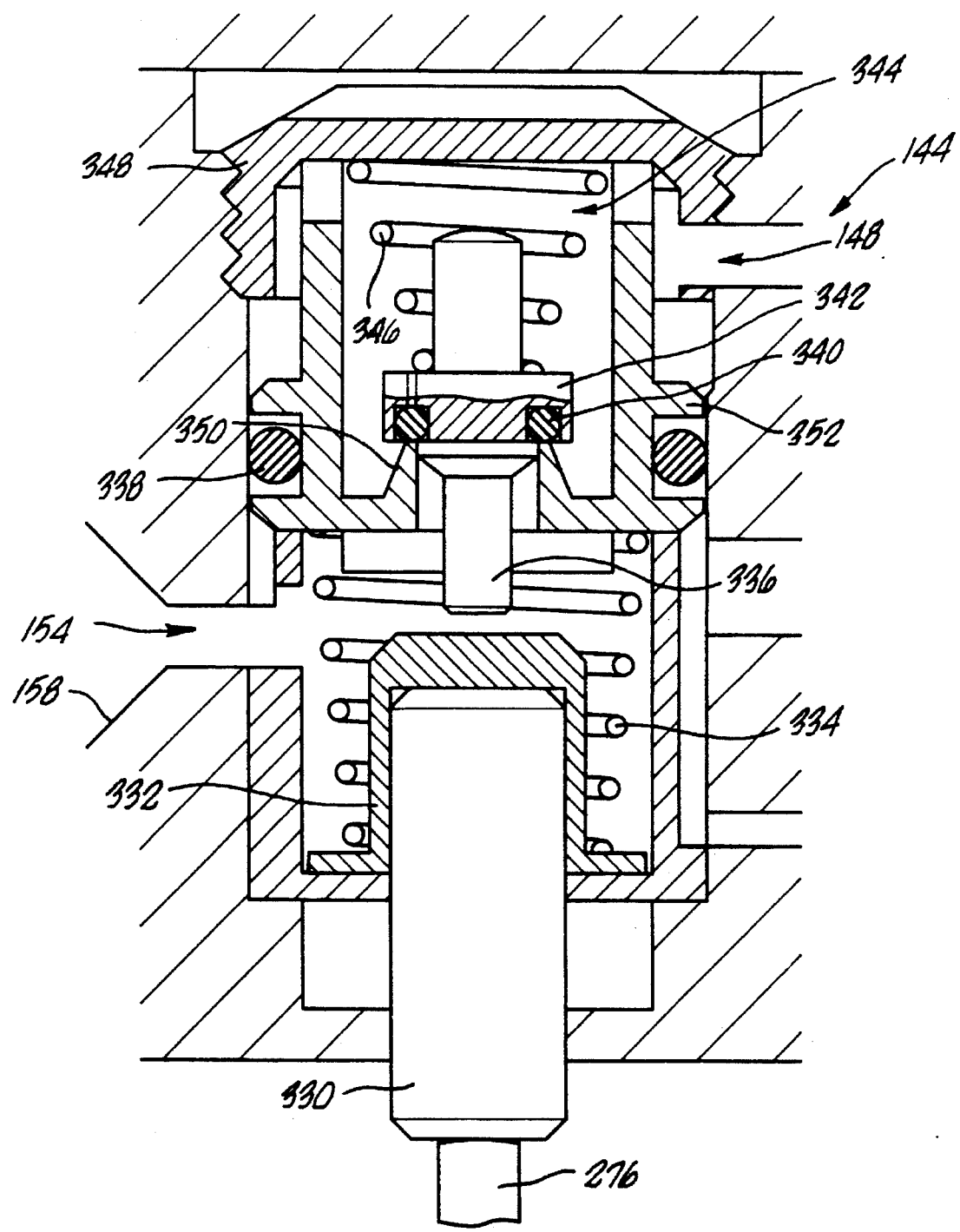
FIG. 7 is an enlarged section view fragment of the initiator valve.

The initiator valve 144, as shown in more detail in FIG. 7, has an initiator valve pin 330 extending from a pin socket 332. A socket spring 334 overlying the pin socket 332 biases the initiator valve pin 330 outwardly or downwardly into engagement with the set screw 276 in the initiator valve cam 274. A valve stem 336 spaced slightly apart from the pin socket 332 has a stem collar 342 with a rubber seat ring 340 sealably engaging a seat neck 350, within an upper chamber 344 of the initiator valve 144. A stem collar spring 346 positioned in between a valve nut 348 and the stem collar 342 biases the seat ring 340 into engagement with the seat nut 350 to maintain the valve 144 in a closed position. The seat nut 350 is supported by, or part of a valve seat 352 sealed within the initiator valve chamber 146 by an o-ring 338.

As shown in FIG. 6a, in an alternate preferred design, the housing is a single piece housing 303, rather than the two-piece housing shown in FIG. 2.

An alternative preferred design to the exhaust valve shown in FIG. 6 is illustrated in FIG. 6b wherein a valve stem 291 slides inside of a front seal 293 and a rear seal 295. A seal spacer 297 separates the front seal 293 and the rear seal 295. The rear end of the valve stem 291 has two narrow slots 305 which provide a channel for flow of gas when the valve is opened, while giving support to the pressurized rear seal 295 to prevent it from collapsing inwardly. The slots 305 form a gradual angle with the rear seal 295 to prevent it from catching on an abrupt edge which could damage the seal. When actuated, the valve stem 291 is pushed forward and the front edge of the valve slots 305 moves forward to the forward edge of the rear seal 295. This allows pressurized exhaust gas to flow from an inlet port 307, through the seal spacer 297, out of the valve slots 305, through a muffler 309 and into an outlet port 311. The front and rear seals 293 and 295 are both u-cup type seals to provide for low friction. The exhaust valve is virtually gas tight and requires very little force for actuation. The only significant force that is translated to the valve stem is after opening, the stem is forced to open further which assists in returning the actuator of the injector.

Figure 6C:
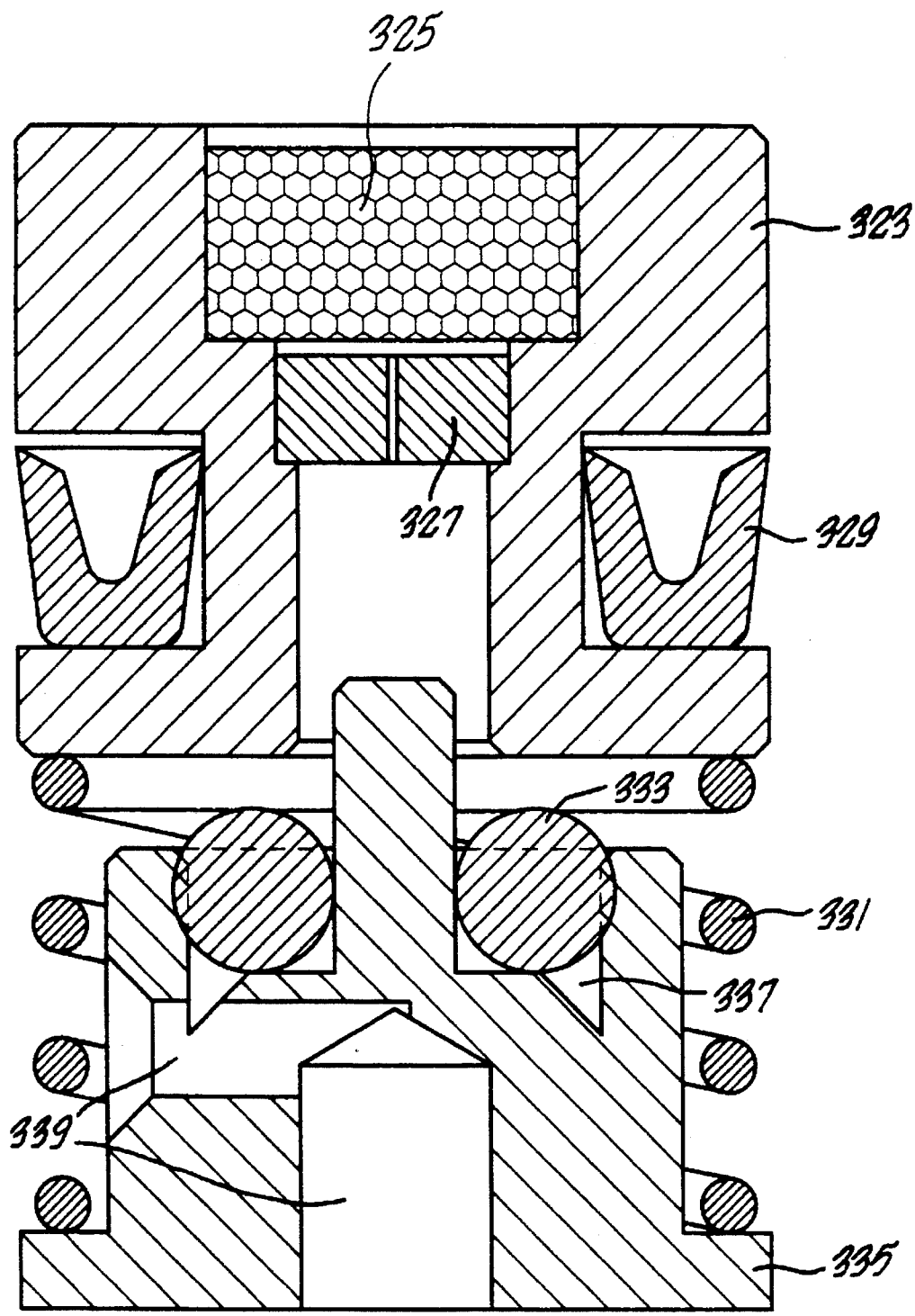

FIG. 6c shows a piston plenum shut-off valve 321 used in the housing 303, as an alternative to the continuously venting orifice 282 and drive plenum exhaust bore 284 shown in FIG. 6. Shut-off valve 321 includes a piston 323 which has a filter 325, an orifice 327 and a seal 329. The piston 323 is biased upwardly and into an open position via a spring 331. When the main piston space is pressurized during the first millisecond of the injection event, and when the pressure reaches approximately 50 psi, the pressure drop across the orifice 327 acts against the piston 323 and drives the piston 323 downwardly against a shut-off seal 333. After the piston 323 seals against the shut-off seal 333, the force keeping the piston 323 down against the seal is provided by the pressure acting on the area of the annulus created by the piston seal 329 and the shut-off seal 333. The shut-off seal 333 is supported by a valve base 335 which has a vent 337 beneath the shut-off seal 333 to prevent seal escape due to trapped gases. Passageways 339 are provided for venting gas. When the pressure acting on the valve is reduced to approximately 50 psi or below, the piston 323 moves away from the shut-off seal 333 due to force provided by a spring 331, and gas flows freely through the filter 325, the orifice 327, and through the passages 339 in the valve base 335. The shut-off valve 321 conserves gas during the injection and provides improved gas efficiency. Comparative testing shows a 30–50% improvement in gas efficiency over the passive orifice design shown in FIG. 6.

Figure 7A:
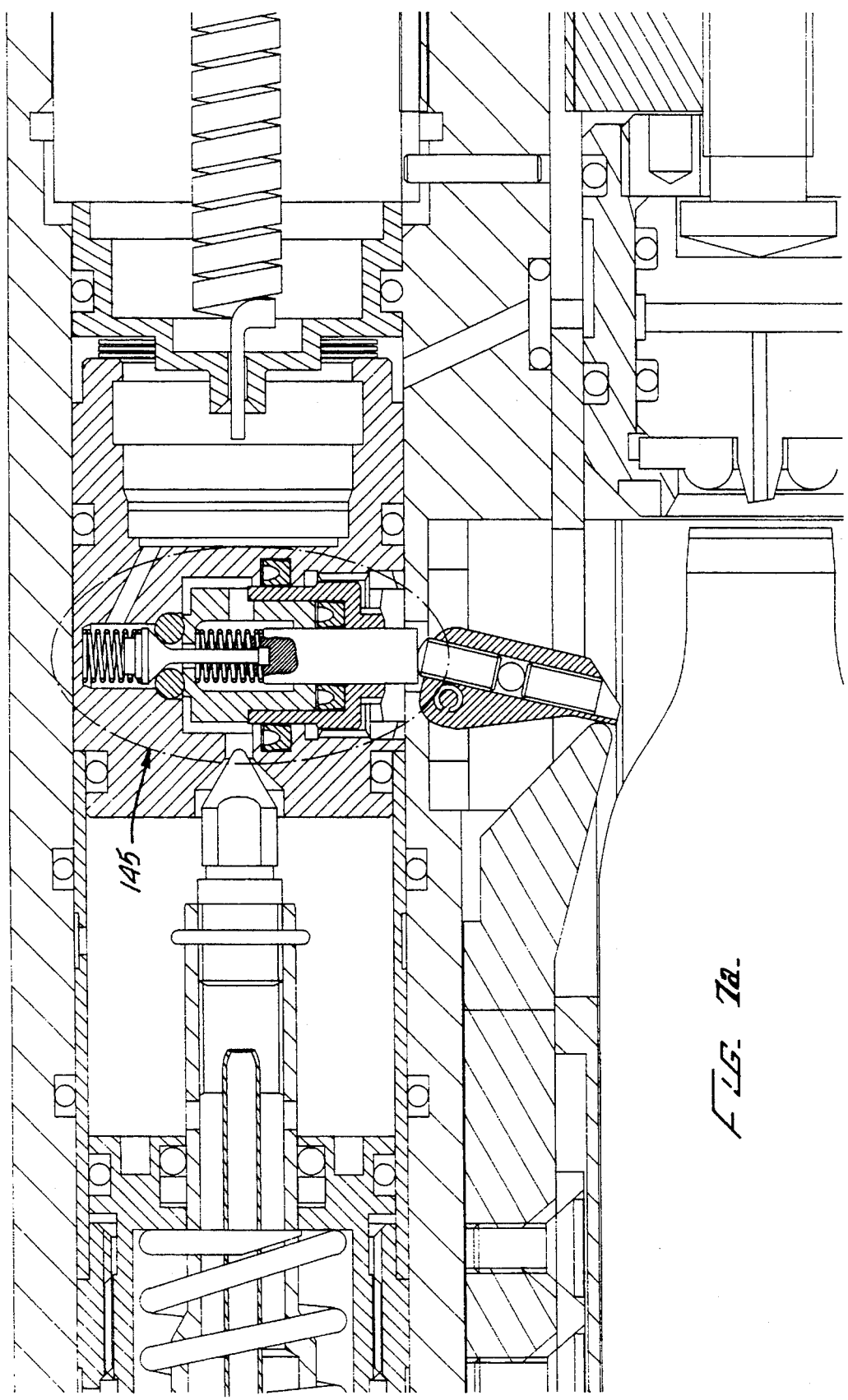
FIG. 7a is a section view fragment of an alternate preferred initiator valve body.
Figure 76:
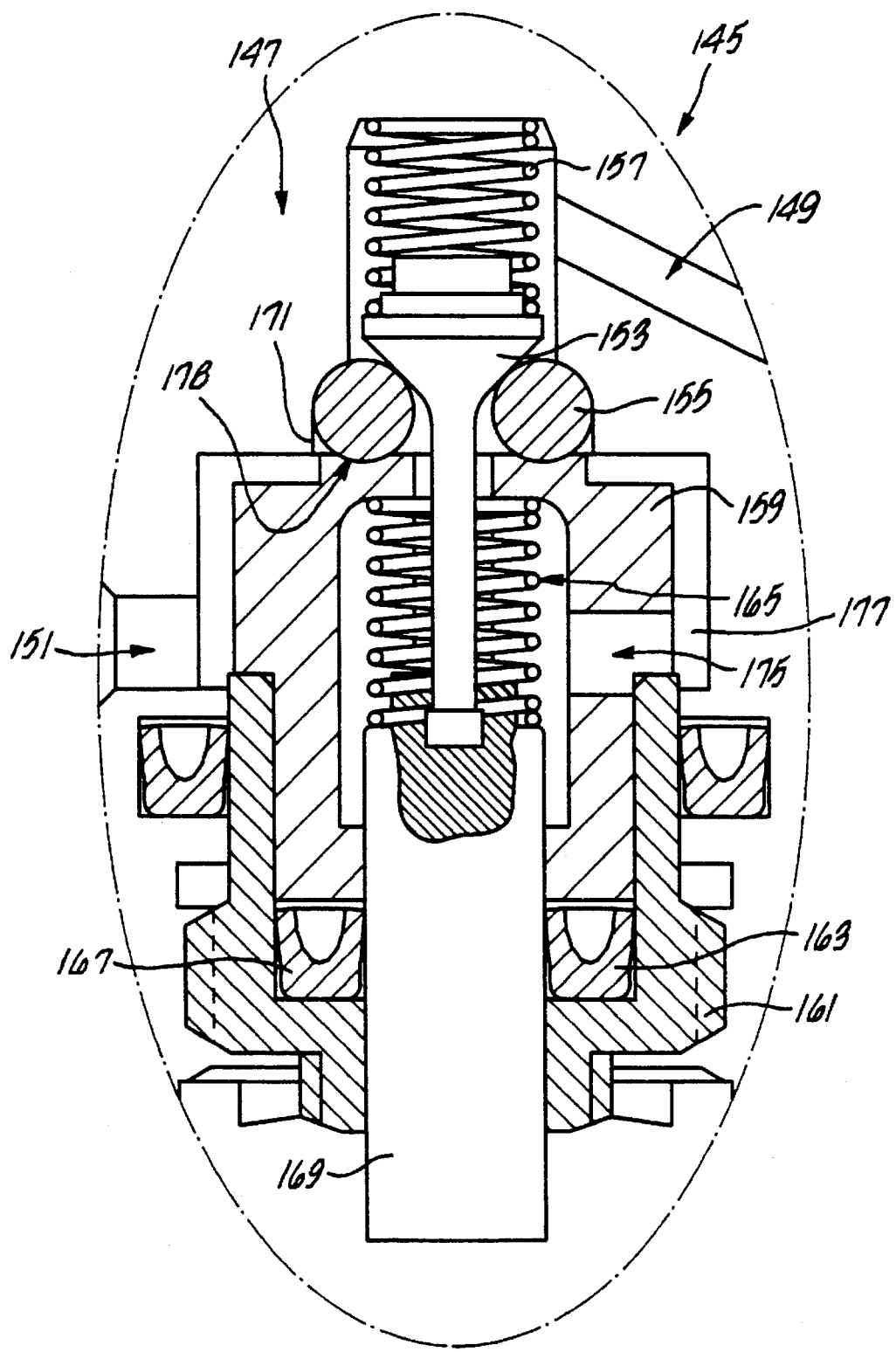

FIGS. 7a and 7b show an alternate preferred embodiment initiator valve 145 (illustrated in the closed position). The initiator valve 145 includes an initiator valve body 147 having an inlet 149 and an outlet 151. A valve poppet 153 is biased against a valve seat 155 by a spring 157. The valve seat 155 is preferably a high durometer ethylene-propylene which resists absorption by carbon dioxide. A valve seat retainer 159 supports the valve seat 155. A valve stem 169 passes through a valve stem guide 161 and a valve stem seal 163. A valve stem spring 165 biases the valve stem into a closed position. A valve stem seal 167 slidably seals the valve stem against the valve stem guide 161. The valve stem seal 167 is preferably a u-cup seal to provide a low break out friction force.

As shown in FIG. 10, an ampule 360 has three spaced apart lugs 382 at its back end. A flare 380 leads into an ampule chamber 384 to guide a contoured end 364 of a plunger 362 to engage the ampule 360. In between the contoured end 364 and a plunger head 370 of the plunger 362 are an o-ring 366 and a split Teflon back up ring 368.

As shown in FIG. 11, the plunger shaft 372 has a cruciform cross section to provide a high moment of inertia using minimum material for the disposable plunger and ampule. A collar 374 on the plunger 362 is spaced apart from the tip of the contoured end 364 so that the collar 374 contacts the back surface 388 of the ampule 360 just before the contoured end 364 of the plunger 362 reaches the front end of the ampule 360. This prevents the contoured end 364 from colliding with the front end of the ampule 360 and overstressing the ampule or buckling the plunger shaft 372. Webs 376 extending from the plunger shaft 372 support the collar 374. Although the back section 390 of the plunger shaft 372 may have teeth or ridges 378 matching the teeth or ridges 240 on the inside surfaces of the clamp jaws 236, a smooth back section 390 is preferred to avoid variations.

Preferred dimensional relationships of parts are shown in the drawings. As an example, the drive piston 212 outside diameter is preferably 1.125 inch.

In operation, the cartridge 54 is loaded into the injector 20 by removing or unsnapping the plastic cartridge chamber cover 56, placing the cartridge 54 into the cartridge chamber 50, with the neck of the cartridge 54 facing the piercing point 68, and then replacing the cartridge chamber cover 56. The cartridge chamber cover 56 snaps into position on the lower housing 44. A wavy brass liner 32 may be provided in the cartridge chamber 50 to increase thermal conductivity between the cartridge 54 and the injector 20.

Referring to FIGS. 2 and 3, the flip handle 80 on the knob 78 is flipped outwardly so that the knob 78 can be more easily turned. The knob 78 is turned by hand causing the threaded shaft 72 to advance forwardly and drive the piercing body 66 and housing 58 towards the cartridge 54. As the piercing body 66 approaches the neck of the cartridge 54, the seal 64 engages and seals against a perimeter on the flat end surface of the cartridge 54. As the user continues to turn the knob 78, the piercing point 68 engages and pierces the cartridge seal. Compressed gas from the cartridge 54 flows through the bore 70, into the annulus 62, through the hole 92 and moves through the bore 96 into the gauge chamber 122. The seal 64 prevents leakage of compressed gas into the cartridge chamber 50 which remains at ambient pressure. The cartridge seat 52 supports the cartridge 54 longitudinally against the force exerted by the seal 64 and piercing pin 68. O-rings 60, 88 and 94 prevent leakage from the passageways from the cartridge 54 to the gauge chamber 122. This relatively long supply path through highly thermally conductive materials or metal components improves heat transfer to the saturated $CO_2$, to reduce the amount of liquid $CO_2$ entering the gauge chamber 122. The heat transfer helps keep the cartridge pressure up, which otherwise tends to drop with each injection due to cooling, caused by expansion of gas out of the cartridge.

As the piercing body 66 and housing 58 slide forward within the lower body to pierce the cartridge 54, the knob 78 moves forward towards the piercing housing nut 76. With the piercing body 66 fully sealed and engaged against the cartridge 54. The piercing body 66 and housing are in a fully forward position and the back surface of the knob 78 is approximately flush with the back surface of the upper housing 42.

Compressed gas fills the gauge chamber 122, passes through the filters 130 and 132, flows through the port 148 (FIG. 3) and into the upper chamber 344 of the initiator valve 144 (FIG. 7). Within the initiator valve 144, the stem collar spring 346 biases the seat ring 340 on the stem collar 342 against the seat neck 350, thereby sealing the upper chamber 344 and preventing the compressed gas from moving forward.

The cartridge 54 contains a saturated propellant gas, such as $CO_2$, in both liquid and gas states, at temperatures near room temperature. The filters 130 and 132 substantially prevent any liquid from the cartridge 54 from passing. This allows the device to be used in any orientation without affecting injection characteristics. Without the filters, liquid $CO_2$ could pass into the initiator valve 144 and reservoir 168 and flash into gas during actuation of the injector 20, causing unpredictable injection characteristics.

As compressed gas fills the gauge chamber 122, the Bourdon tube 116 which opens into the gauge chamber 122 is also pressurized. The pressure within the Bourdon tube 116 causes it to spiral outwardly resulting in movement of the pointer 102 to indicate the gas pressure on the gauge label 104 (after the gauge body 106 and gauge base 114 have been properly calibrated). The user can then check the available gas pressure within the injector 20 by looking at the pointer 102 through the lens 98, as shown in FIG. 8.

The ampule 360, plunger 362 and a filling needle may be provided in a sterile package. The filling needle has a fitting to engage the Luer fitting 392 on the ampule. The ampule may be filled in the same way as a conventional needle and syringe. The filling needle is inserted into a vial of injectant and the injectant is drawn up into the ampule by pulling back on the plunger. Dosage is read by the alignment of the red o-ring 366 with volume graduations on the transparent ampule. The filling needle is removed and safely discarded. The ampule is then ready to be placed into the injector. Variable dosage injections are accordingly achieved by loading the ampule in the same manner as for a needle and syringe. In contrast to other injectors, the present injector 20 can inject various dosages without adjusting the injector. The ampule 360 may be filled to e.g., ⅓, ½, ¾, etc. of its full volume capacity. Referring to FIG. 10, loading the ampule 360 with differing volumes of injectant will cause the plunger 362 to extend from the ampule 360 by varying amounts. However, since the injector 20 can successfully drive the plunger 362 from any plunger starting position, a single size ampule 360 can be used for various dosage injections. Ampules of varying volumes are not required.

With the ampule 360 loaded with the desired dosage and the plunger 362 extending from the ampule 360, the plunger and ampule are installed into the injector 20. The lugs 382 on the ampule 360 are aligned to pass through the lugs 254 on the front collar 252. The back end of the plunger 362 is passed through the front collar 252, through the return spring 44 and through the clamp piston spring 224. Since the teeth or ridges 378 on the plunger 362 extend continuously in between the webs 376 and the back end of the plunger, regardless of the dosage carried by the ampule 360, the teeth 240 of the clamp jaws 236 will over lie the plunger 362.

The back surface 388 of the ampule 360 comes to rest against the pressure plate 248. The lugs 382 on the ampule 360 fit in between the lugs 258 on the indicator ring 250. The user then turns the ampule (clockwise as viewed from the front) through an acute angle e.g., approximately 45°, from an ampule loading position to an ampule ready position. As the ampule turns, it causes the indicator ring 250 to turn with it as the sides of the ampule lugs 382 push against the sides of the indicator ring lugs 258. A step on each ampule lug prevents the indicator ring and ampule from being turned beyond range. In addition, as shown in FIG. 13a, the track on which the detent pin 288 acts is deep enough that the detent cannot be forced out of the track. The two ends of the track act as detent stops. As the indicator ring 250 turns and locks into an injection ready position (FIG. 2a), the colored or painted sections on the outside perimeter of the indicator ring 250 moves into view through the view ports 256. This indicates to the user that the ampule is properly installed in the injector 20 and ready for injection.

As the indicator ring 250 turns with the ampule 360 from the ampule loading position to the ready position, a cut out 320 in the indicator ring (FIG. 13) moves into alignment with the hook 264 on the actuator link 262. The trigger 30 can then be pulled back to actuate the injector 20 to provide an injection to a patient.

If the cut out 320 in the indicator ring 250 is not aligned with the hook 264, the actuator link 262 prevents the trigger 30 from moving to actuate the device. Therefore, the injector 20 cannot be actuated unless an ampule is properly installed and aligned in the ready position. With a cartridge 54 and an ampule 360 properly installed within the injector 20, the nozzle 386 of the ampule 360 is placed against the patient's skin and the trigger 30 on the actuator slide block 266 is pulled back by the user's index finger. As the slide block end 272 approaches the initiator valve cam 274, the exhaust valve fork 270 slides the spool valve 286 from an open position (which allows the reservoir 168 to bleed or exhaust through the exhaust bore to ambient) to a closed position wherein the spool valve 286 substantially seals off the reservoir exhaust bore 290. The reservoir 168 is accordingly sealed off before the slide block end 272 engages the initiator valve cam 274. The spool valve serves as an exhaust control valve.

As the actuator slide block 266 continues to move rearwardly, the slide block end 272 pushes against the initiator valve cam 274 levering the set screw 276 against the initiator valve pin 330. The lever arm design of the initiator valve cam 274 provides an approximately 4:1 mechanical advantage. This reduces the force necessary to pull the trigger 30 back to actuate the device. On the other hand this mechanical advantage also incurs a 4:1 travel loss, which is advantageously employed in timing the operation of the initiator valve and spool valve, through adjustment of the set screw 276. The close tolerance and low leakage fit between the spool valve 286 and spool housing 294 add only a negligible amount of frictional drag on the trigger 30. There are no soft seals which slide with the trigger. The sliding movement of the trigger performs three functions: It controls the initiator valve, it controls the spool valve, and it provides an interlock when disabled by the actuator link 262. The absence of sliding elastomer seals on either the initiator valve or the spool valve and the 4:1 mechanical advantage of the initiator valve cam 274 allow both of these high pressure valves to be operated with minimum finger force on the trigger.

Referring to FIGS. 3 and 7, as the actuator slide block 266 moves against the initiator valve cam 274, the set screw 276 pushes up on the initiator valve pin 330. The pin socket 332 is driven up against the valve stem 336 causing the stem collar to shift upwardly and separate the seat ring 340 from the seat neck 350, thereby opening the initiator valve 144. Similarly, in the embodiment of FIGS. 7a and 7b, the valve poppet spring 157 biases the valve poppet 153 toward the valve seat 155. Gas pressure from the gas inlet 149 drives the poppet 153 into the valve seat 155 creating a gas tight seal. The valve seat 155 is vented on the bottom side 171 to prevent the seat from escaping from the groove 173 due to trapped gases. The valve seat retainer 159 retains and vents the valve seal 155. The valve stem 169 is mechanically isolated from the poppet 153 to assure that the poppet closes without interference from the stem.

When the initiator valve 147 is actuated, the valve stem 169 slides up and contacts the valve poppet 153, pushing it away from the valve seat 155. Gas flows from the inlet 149 through a gap between the valve poppet and valve seat, through a side hole 175, around an annulus 177, and out through the outlet 151. When the valve stem is released, the valve stem spring 165 returns the valve stem to the neutral position and the valve poppet 153 also returns to the closed position.

Referring once again to FIGS. 3 and 7, with the initiator valve 144 opened, compressed gas flows from the cartridge 54 through the filters and initiator valve 144, through the reservoir port 154 past the dart 160 and into the reservoir 168. Referring to FIGS. 3 and 5, as the reservoir 168 fills with compressed gas, gas pressure also builds within the poppet chamber 208, as gas flows from the reservoir 168 through the poppet body supply holes 174.

Since the cannula 176 is opened to the reservoir 168, compressed gas flows from the reservoir 168 through the cannula 176 into the clamp piston plenum 216.

Figure 2B:
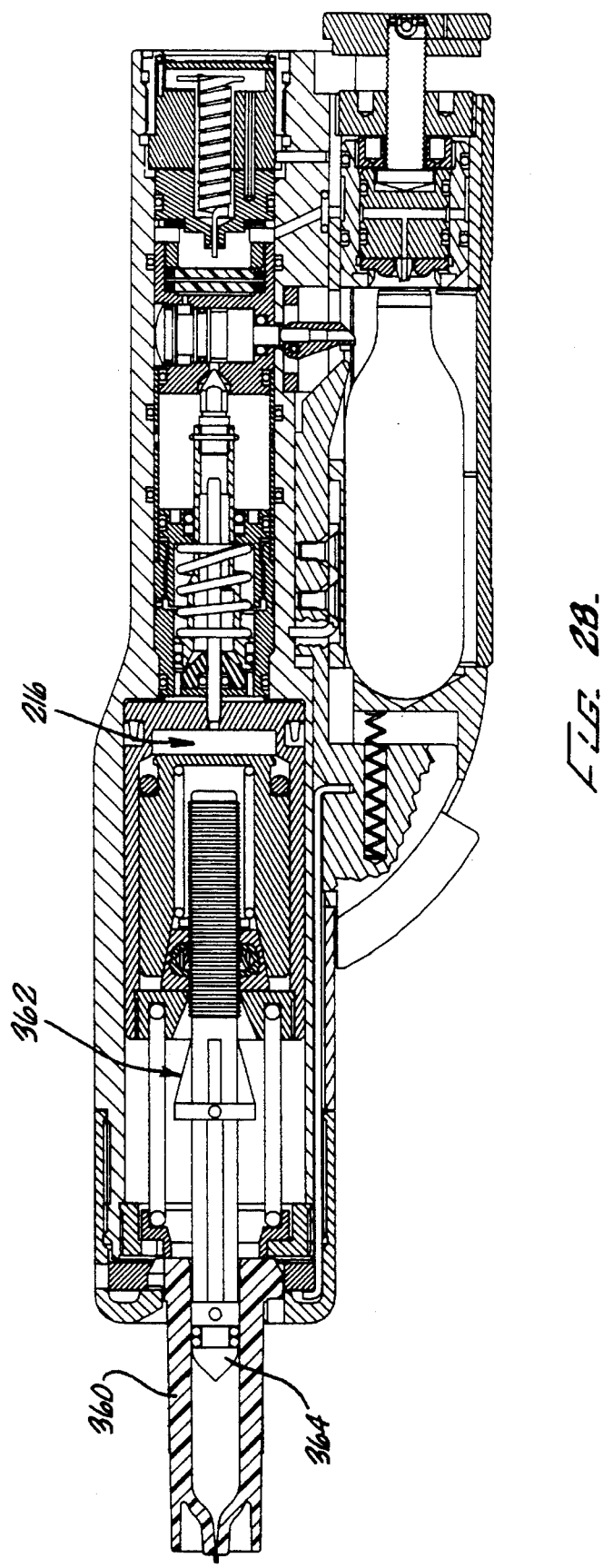
FIG. 2b is a section view thereof illustrating a clamping mechanism of the device in a pre-injection position.

Referring to FIGS. 2b and 4, as pressure builds within the clamp piston plenum 216, the clamp piston 210 is driven forward compressing the clamp piston spring 224 and driving the clamp jaws 236 together, through the interaction of the ramp drive 232 on the clamp piston 210 and the clamp piston ramps 234 on the clamp jaws 236. The teeth 240 on the clamp jaws 236 clamp down and around the plunger With or without teeth on the plunger, the jaws engage the plunger with enough gripping force to avoid any slippage between the jaws and plunger during actuation of the injector.

The clamp jaws 236 and their driving mechanism perform two functions: They grab onto the plunger at whatever position the plunger is in, and they transfer driving force from the drive piston to the plunger.

Figure 12:
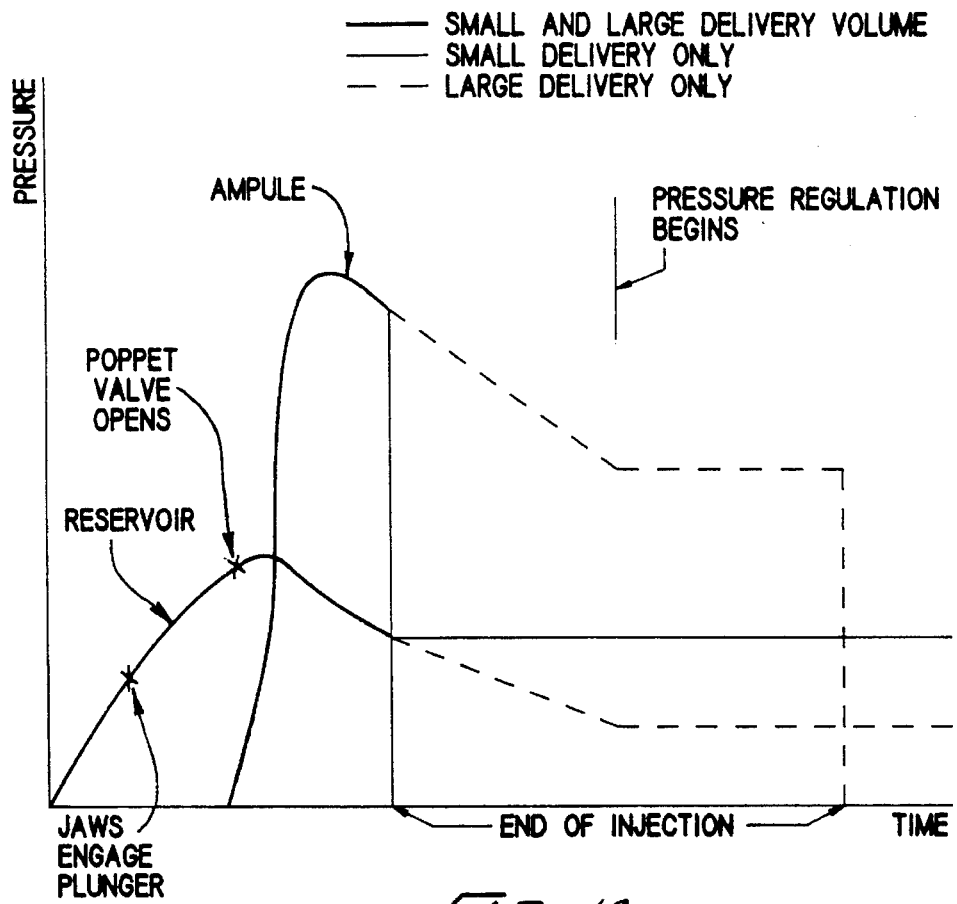
FIG. 12 is a graphic illustration of operation of certain features of the present device.

If the ampule 360 is loaded with a maximum volume, the plunger 362 will be fully extended to the rear such that the clamp jaws 236 will engage the plunger 362 close behind the webs 376. On the other hand, if the ampule 360 is loaded with a minimal dosage, the plunger 362 will extend a shorter distance behind the ampule 360 and the clamp jaws 236 will engage the plunger 362 towards the back end of the plunger. However, regardless of the volume of the injectant in the ampule, the clamp jaws 236 securely clamp and engage the plunger 362 with the teeth 240 on the clamp jaws 236 locked into the teeth 378 on the plunger 362. The gas pressure in the clamp piston plenum 216 maintains the engagement of the clamp jaws 236 to the plunger 362 during the injection sequence. As represented in FIG. 12, the clamp jaws clamp onto the plunger before the poppet valve opens.

Referring to FIGS. 3, 4 and 5, pressure in the poppet chamber 208 continues to build until it is sufficient to crack the poppet valve 170 open. Specifically, the poppet spring chamber 226 is sealed from the reservoir 168 and the poppet chamber 208 and is vented to ambient pressure. As pressure increases within the poppet chamber 208, the rearward acting force resulting from the gas pressure acting on the incline surfaces 152 of the poppet body 172 will exceed the forward acting force of the poppet spring 186. When this "cracking point" is reached (preferably at approximately 450 p.s.i.), the poppet valve 170 snaps open. The poppet body 172 shifts or slides rearwardly. The sealing edge surface 200 separates from its sealing engagement against the conical poppet seat 188 allowing gas from the reservoir 168 to flow through the poppet chamber 208 to the drive bores 194. As the poppet valve 170 begins to open and the poppet body 172 moves away from the conical poppet seal 188, the annular front surface 230 of the poppet body 172 is acted on by gas pressure now in the poppet annulus 198. Since the surface areas acted on by the compressed gas are vastly increased with the addition of the front surface 230 of the poppet body, the force acting on the poppet body 172 rapidly escalates. The poppet valve 170 therefore opens with an "over-center" or hard-over action. When the poppet valve 170 opens and the poppet body 172 shifts rearwardly, the regulation valve 156 closes down via the dart 160 engaging and sealing against the regulation seat 158. Thus, additional gas supply to the reservoir 168 is, at least initially, restricted by the regulation valve 156, with substantially only the reservoir 168 then acting as a source of compressed gas.

To maintain at least the minimum pressure on the drive piston throughout the injection, pressure regulation of the reservoir is provided through poppet area ratios and spring forces (which may be readily determined for various capacity injectors by those skilled in the art). During injection of larger dosages, the reservoir pressure reaches a desired minimum pressure. Up to this time, the drive piston plenum has been supplied by a fixed supply of gas from the reservoir. At this point, the spring force, acting forwardly on the poppet body, overcomes the net pressure force, acting rearwardly on the poppet body. As the reservoir pressure drops below this value preferably approximately 150 p.s.i., the poppet body moves forward, lessening the regulation valve restriction to incoming flow. Specifically, the dart 160 moves with the poppet body away from the seat 158 to allow commencement or increase of gas flow. Thus, the opening of the regulator valve consequently increases gas flow into the reservoir and increases the reservoir pressure. As gas pressure then increases above the desired minimum value, the poppet body again moves rearwardly to restrict the incoming flow. Thus the poppet valve and regulator valve act together as a reservoir pressure regulator (and consequently drive piston plenum pressure and ampule pressure). Actual physical movement of the poppet body from fully open to full closure of the regulator valve is approximately 0.020 inch. Referring to FIG. 12, regulation movement, when present, occurs generally during the last half of the injection.

With this pressure regulation technique, the reservoir volume may be reduced, thus less gas is used, especially during smaller deliveries. In addition, the regulation/small reservoir combination, as compared to fixed volume/no regulation, results in smaller final pressures for smaller dosages of deliveries and larger final pressures for larger dosages. Thus final pressures are less dependent on dosage volume and ampule pressures are more consistent, which provides for more uniform injections.

The $CO_2$ cartridge is filled with saturated $CO_2$. Thus the source pressure is highly dependent on temperature (varying roughly 10 psi/deg F.). The peak ampule pressure is determined by the poppet valve cracking pressure which is independent of source pressure. The minimum delivery pressure, governed by the pressure regulation is also independent of source pressure. Both of these features are controlled by area ratios and spring rates. Thus the injector is substantially temperature independent.

Certain known injectors can apparently provide variable dosage by pulling the plunger only part way back, leaving a gap between the drive piston and the plunger. With this technique, however, the drive piston must then travel across the gap before contacting the plunger, altering the piston momentum and dead volume parameters of the device, and substantially effecting ampule pressure characteristics. With the present clamping mechanism, dead volume and piston momentum are independent of dosage, and consistent ampule pressure characteristics are maintained.

FIG. 12 illustrates the effect of pressure regulation. With a smaller dosage of e.g., ½ ml or less, generally there is no pressure regulation. With larger dosages of e.g., over ¾ ml, pressure regulation occurs. With intermediate range dosages of e.g., between ½ and ¾ ml, some pressure regulation may occur.

The poppet annulus 198 and drive bores 194 create a "dead volume" which should be minimized for preferred injection characteristics i.e., rapid pressure build up and acceleration of the plunger. However, the flow restrictions or pressure drops caused by the poppet annulus and drive bores 194 are preferably also minimized for the same reason. In a preferred embodiment, ten equally radially spaced apart drive bores 194 are provided through the front surface of the poppet housing 178.

The rubber or elastomeric face seal 196 adhered to the back of the drive piston 212 assists to rapidly open the poppet valve 170. The face seal 196 encourages the build up of pressure in the drive bores 194 and poppet annulus 198 before pressurizing the drive plenum 202. The "dead volume" of the drive plenum 202 is therefore eliminated by the drive bore seal 196. Accordingly, the rapid pressure increase within the drive bores 194 and poppet annulus 198 shorten the time required for opening the poppet valve 170 providing a quick ampule pressure rise time and a more uniform ampule peak pressure. The poppet body supply holes 174 have a large diameter to minimize pressure drop from the reservoir 168 to the poppet chamber 208.

Figure 2C:
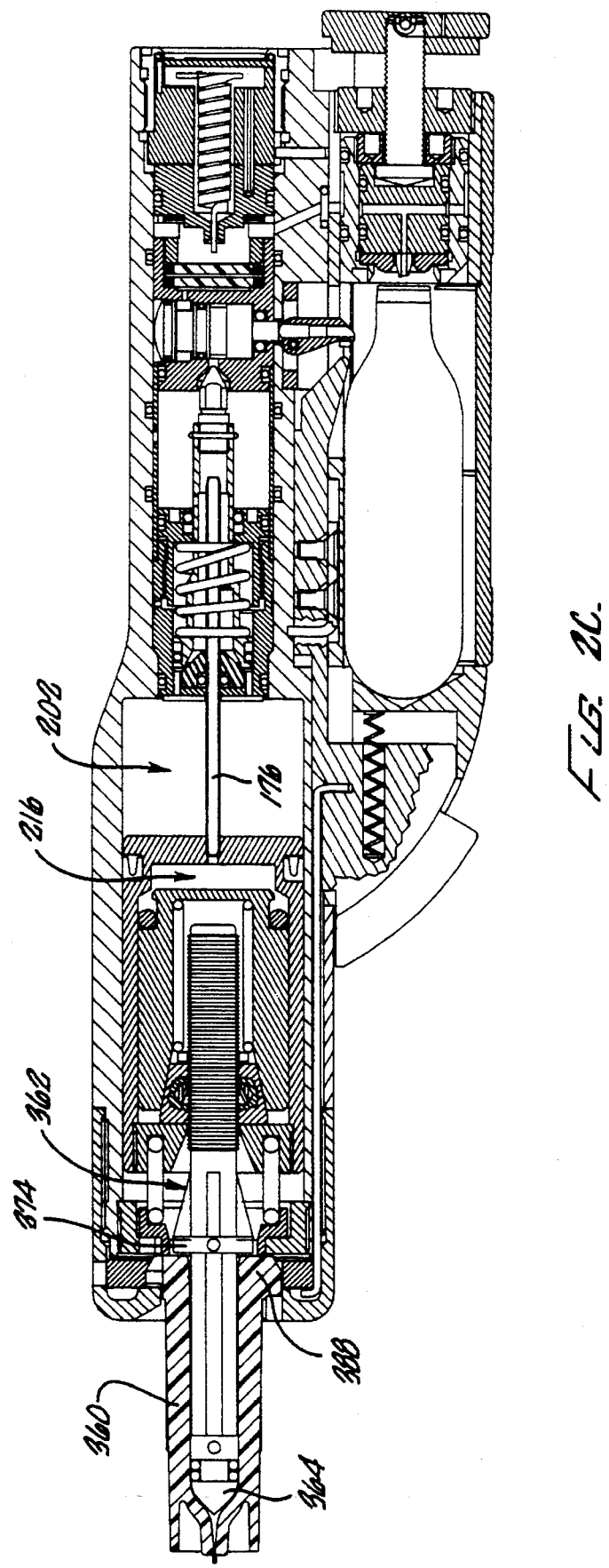
FIG. 2c is a section view thereof illustrating a drive piston, clamping mechanism and plunger in a post-injection position.

With the poppet valve 170 open, gas flows through the poppet annulus 198 and drive bores 194 into the drive plenum 202. The gas pressure in the drive plenum 202 acting on the relatively large surface area of the entire back surface of the drive piston 212 generates a large force on the drive piston 212 in the forward direction. The drive piston 212 accelerates forward with the clamp piston 210 driving the plunger 362 into the ampule 360. The injectant dose within the ampule chamber 384 is sprayed out of the ampule nozzle 386 in a high velocity jet which penetrates through the patient's skin. FIG. 2c shows the position of the plunger 362 and piston 212 after injection.

If the trigger 30 is held back for longer than necessary for the injection, only a small amount of gas is wasted since all spaces within the injector, except the drive plenum, remain virtually sealed while the trigger is held back. The drive plenum is opened to ambient pressure, but only through orifice 282 which severely restricts flow. The regulation valve 156 restricts flow while the trigger is held back.

After the injection, the trigger is released. The slide block spring 268 assisted by exhaust gas pressure returns the slide block 266 to its forward position. The initiator valve then closes. Then the exhaust valve fork 270 moving with the slide block 266 pulls the spool valve 286 forward reconnecting the spool valve bore 302 and spool plenum 300 to the reservoir exhaust bore 290. The spool valve and exhaust passage allow the injector to be quickly and quietly reset for another injection. Gas in the reservoir exhausts out through the reservoir exhaust bore 290 and exhaust passage 296. As this occurs, the exhaust gas pressure in the exhaust passage 296 pushes on the back of the spool valve 286 and helps to return the spool valve and slide block forward to their original ready positions. The slide block spring 268 consequently need only exert a slight force, thereby helping to reduce the finger force necessary to pull the trigger 30.

Immediately after the injection, the drive piston 212 is in the forward position (FIG. 2c), with the plunger shoulder in contact with and exerting a large force on the back end 388 of the ampule 360. The drive piston return spring 244, clamp piston spring 224 and jaw springs 238 are compressed. The jaws 236 are engaged with the plunger and the clamp piston 210 is forward. Each part must then return to the ready position.

Upon release of the trigger 30, the reservoir 168 is able to rapidly vent to atmosphere. Drive piston plenum gas vents into the reservoir, in part, through the poppet body, until the poppet valve closes. Gas also vents into the reservoir through the cannula 176, until the holes in the cannula are sealed by the o-ring 190 contained within the poppet seat 188. This remaining gas, which occupies a relatively small volume, and is at a very low pressure, vents through the bleed orifice 282 connecting the drive piston plenum directly to the atmosphere through the drive plenum exhaust bore 284. Since the orifice 282 is always open, even during the injection, some beneficial drive gas is lost, thus it is a very small, restrictive orifice. Because the orifice 282 is small, if it was the only vent for drive piston plenum gas (i.e., if there were no cannula side holes), venting and reset time would be unacceptably long.

During venting, the following reset sequence occurs and is controlled by component areas and spring forces, which may be readily determined by those skilled in the art. First, the clamp jaws 236 and clamp piston 210 release. This must occur before the drive piston is released so that the plunger is not pulled back. The clamp piston spring force overcomes the opposing pressure force. This release occurs when the drive piston 212 is close to a force equilibrium condition. The pressure force must be close to the opposing spring force. If not, then the drive piston 212 will rapidly return (if the spring force is larger) or plunge forward (if pressure force is larger) causing noise and possible damage to the injector. Thus a force balance is established at the point of plunger release, regardless of the dosage.

After the plunger release, the drive piston 212 returns as the reservoir bleeds. The drive piston 212 is forced rearward by the drive piston return spring against the opposing pressure force. Gas exhaust and reset occurs quietly and quickly.

O-ring 222 serves as a seal and a bumper to quiet the clamp piston return.

During the injection, the plunger 362 is driven forward until the collar 374 contacts the back surface 388 of the ampule 360. Accordingly, if the trigger 30 is squeezed once and an injection given, released and squeezed again after some delay (i.e., "second fire") without replacing the ampule, the jaws will grab the plunger with the plunger collar in the forward most position, i.e., in contact with the rear ampule face. Thus no forward movement of the drive piston will occur. A second fire does not damage the ampule, plunger or injector.

The cannula 176 is attached to and moves with the drive piston 212. The cannula exhaust hole 190 in the cannula 176 speeds the return stroke of the piston 212. The poppet valve closes before the drive piston begins its return. Thus a bleed hole in the cannula is required for gas to flow from the drive piston plenum to the reservoir. During the return stroke, up until the time the cannula exhaust hole 190 passes behind the o-ring 206, gas in the drive plenum 202 flows through the cannula exhaust hole 190 through the cannula 176, back into the reservoir 168 and out through the relatively unobstructed exhaust system of the reservoir exhaust bore 290 and the exhaust passage 296. After the cannula exhaust hole 190 passes behind the o-ring 206, the gas remaining in the now very small volume drive plenum 202, which is a very low pressure, is exhausted through the orifice 282 and drive plenum exhaust bore 284 to ambient. Gas in the clamp piston plenum 216 similarly exhausts through the cannula 176 through the reservoir 168 and out through the reservoir exhaust bore 290 and the exhaust passage 296.

The spent ampule and plunger are turned and removed from the injector 20 which is then prepared for the next injection sequence. The ampule and plunger are preferably a single use disposable unit.

Figure 10A:
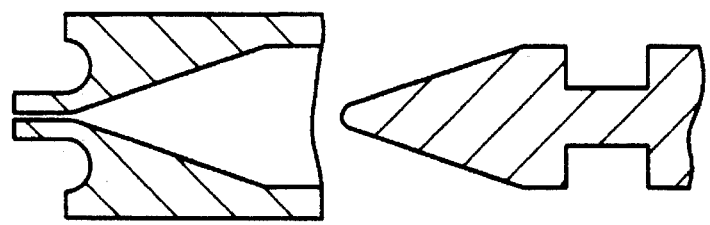
FIG. 10a, 10b and 10c are section view fragments of alternate plunger and ampule embodiments.
Figure 10B:
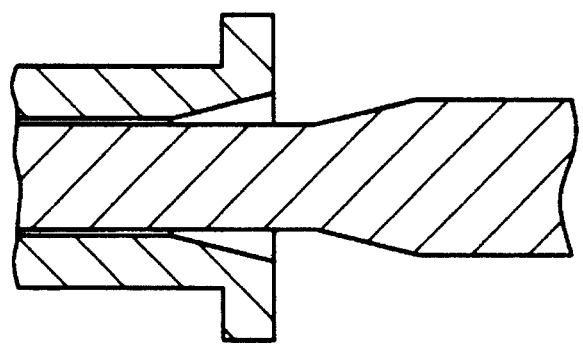
Figure 10C:
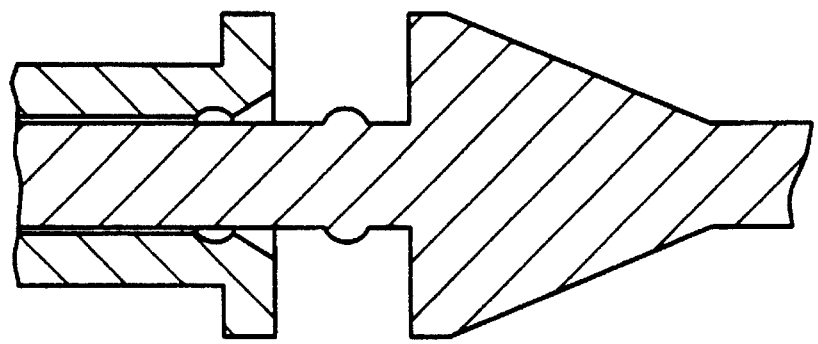

As shown in FIGS. 10a and 10b, the plunger may have tapered sections at the front or back which engage a generally complimentary tapered section in the ampule. During an injection, the injector exerts hundreds of pounds of force on the plunger which drives the tapered section of the plunger of FIGS. 10a and 10b into an interference fit with the tapered section of the ampule. The used and non sterile plunger and ampule cannot easily then be re-used. The tapered sections can also act as a plunger stop, in place of the collar on the plunger of FIG. 10. The taper on the plunger and ampule are slightly mismatched and lock together only with high forces (at the end of an injection) and not at low forces (during filling of the ampule). FIG. 10c shows another nonreusable ampule and plunger having a detent. The detent is dimensioned so that only a large force will cause engagement.

Figure 4B:
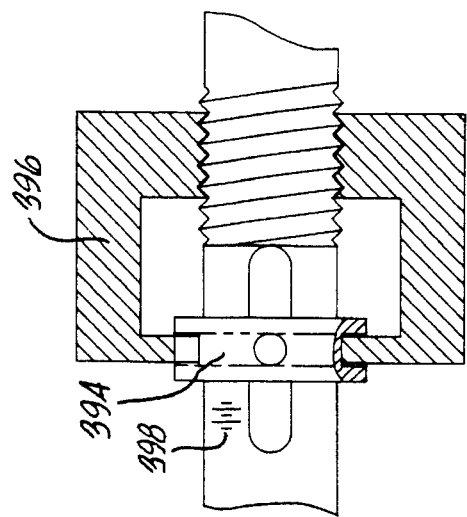
FIGS. 4a and 4b are section view fragments thereof showing an alternate embodiment.
Figure 4A:
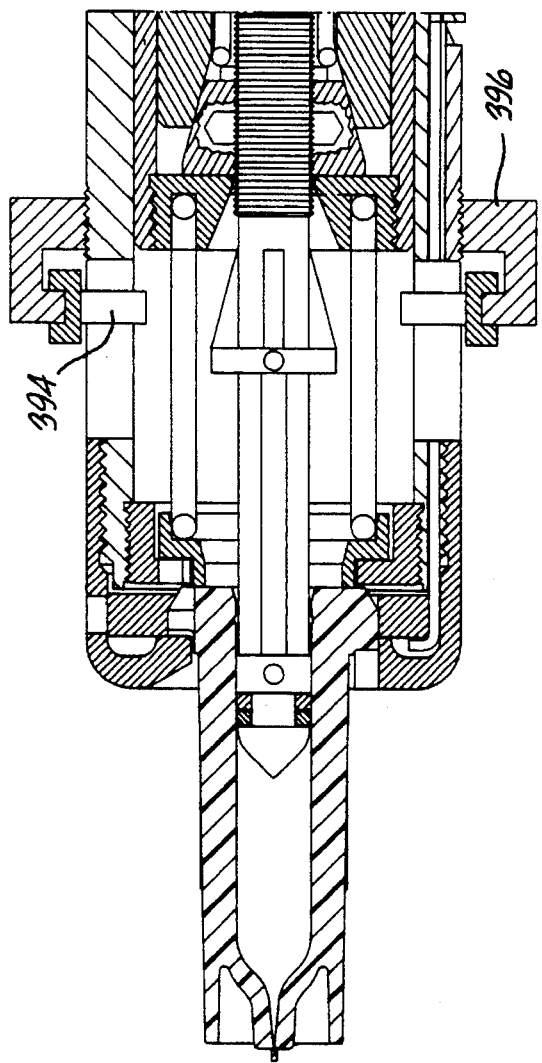
Figure 9:
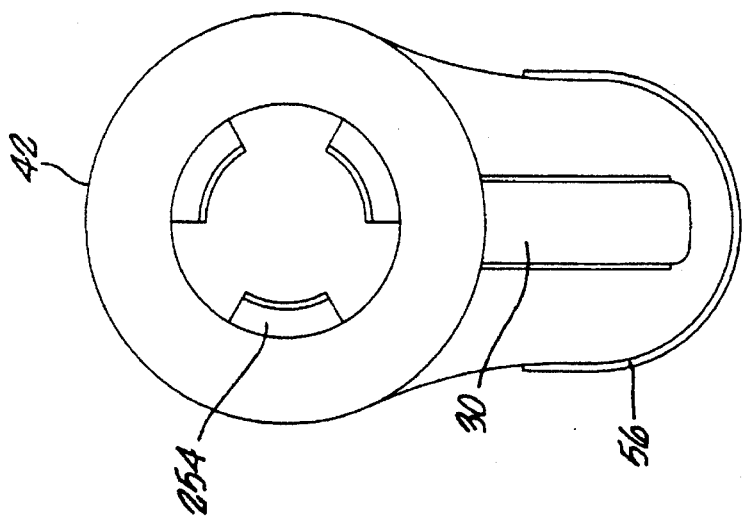
FIG. 9 is a front elevation view thereof.

The injector can be modified to give multiple sequential injections to the same patient. As shown in FIGS. 4a and 4b, a drive piston stop 394 is added, and acts to stop the drive piston, as the plunger shoulder does in variable delivery. When the injector actuates, a small dose is delivered. The jaws then disengage and the injector resets. The plunger will automatically be in a "ready" position for the next shot, and the injector may be fired again to deliver the same small dosage. This sequence may be repeated to deliver several small dosage injections until the plunger shoulder contacts the ampule. Dosage may be adjusted by rotating the outer ring 396 to the desired value, indicated by graduations 398 on the injector housing. A longer ampule can be provided to allow for more sequential shots.

The present method of needleless injection uses a system of an injector and compatible ampules. The injector is designed to apply a specific force on the plunger of the ampules. The force applied to the plunger by the injector is varied, forming a force-displacement curve. At the beginning of the injection, the force applied to the plunger is quite high. As the plunger is advanced, the applied force is reduced substantially linearly until the volume injected reaches approximately 0.5 ml, and thereafter the force is held substantially constant. This force displacement curve is independent of the ampule nozzle size. This force-displacement curve translates directly to an ampule pressure-volume injected curve. The injection system employs a singular pressure profile and a family of ampules with various orifice sizes to achieve various depths of penetration. FIG. 27 shows preferred uses of various diameter nozzles with the pressure profile described below.

The traditional approach to measuring pressure profile is to use a pressure-time curve. However, a pressure-volume profile is particularly useful because this pressure profile is nearly the same for any size nozzle. In the following discussion, both time and volume will be used as a reference.

Referring to FIGS. 25 and 28–30, the preferred pressure profile has the following properties: First the pressure rapidly increases from 0 to a value of about 3900–4300 psi (and preferably about 4100 psi) in less than 6 milliseconds (and preferably less than 1 ms). This quick pressure rise avoids "splash-back" and loss of injectant. This pressure range is sufficient to pierce the tissues, but not so high as to cause the excessive pain associated with higher pressures. The pressure is gradually reduced to approximately 1200–2000 psi (and preferably 1800 psi) in a generally linear (pressure-volume) fashion corresponding with volume discharged of 0.5 ml. In a pressure-time framework, the curve forms an exponential decay. At this point, the pressure is held constant until the end of the injection, at which time the pressure abruptly goes to 0 (optimally in less than 5 ms.) Final pressures below about 1200 psi tend to result in "leak-back" of the injectant after the injection. The pressure profile is defined as the pressure immediately proximal to the nozzle. The above-described pressure profile covers an injection larger than approximately 0.5 ml. If the injection is less than this amount, the pressure-profile curve is simply truncated at the end of the delivered volume.

Medication viscosity affects penetration of intramuscular injections in a direction contrary to prior art. Experimental data shows that more viscous medications, in the range from 0.01 to 0.7 poise, have greater fascia penetrating capability, believed to result from the reduced turbulence, lower Reynold's number, and also apparently due to higher core velocities for viscous injectants as compared to less viscous injectants. Thus, the present invention also includes the appropriate guidelines for selection of nozzle size with viscous medications. Viscous medications preferably use the same size orifice as for water based medications. Nearly all viscous medications are intramuscular injections. Testing shows that viscous medications have more energy to penetrate the deep fascia than water based medications, but do not go substantially deeper into the muscle. Therefore, the deposition into the muscle is comparable independent of medication viscosity.

The present peri-fascial injection is provided by using a nozzle diameter which is smaller than that which would ordinarily be used for an intramuscular injection. The peri-fascial injection is provided by using a SC nozzle (0.004") at an IM injection site preferably with less than 5 mm adipose. This works well because IM sites tend to have very thin layers of adipose tissue. The SC nozzle has sufficient penetrating energy to deposit the medication on the deep fascia when injected into a thin layer of adipose. A peri-fascial injection can also be given at an IM injection site having a 10–15 mm adipose layer using a 0.006 inch diameter nozzle and the above-described pressure profile. As shown in FIG. 26, the injectant 800 in a peri-fascial injection bores through the skin 802 and adipose 804, but not the fascia 806. Rather, the injectant forms a thin layer 808 over the fascia. The thin layer 808 may provide the same pharmacological effect as an IM injection, without penetrating the muscle.

Second Embodiment

In a second embodiment, as shown in FIG. 15, the present needleless injection device 520 has an ampule 360 at its front end. The ampule is held against the patient's skin while the device 520 is triggered to achieve the injection.

Figure 16:
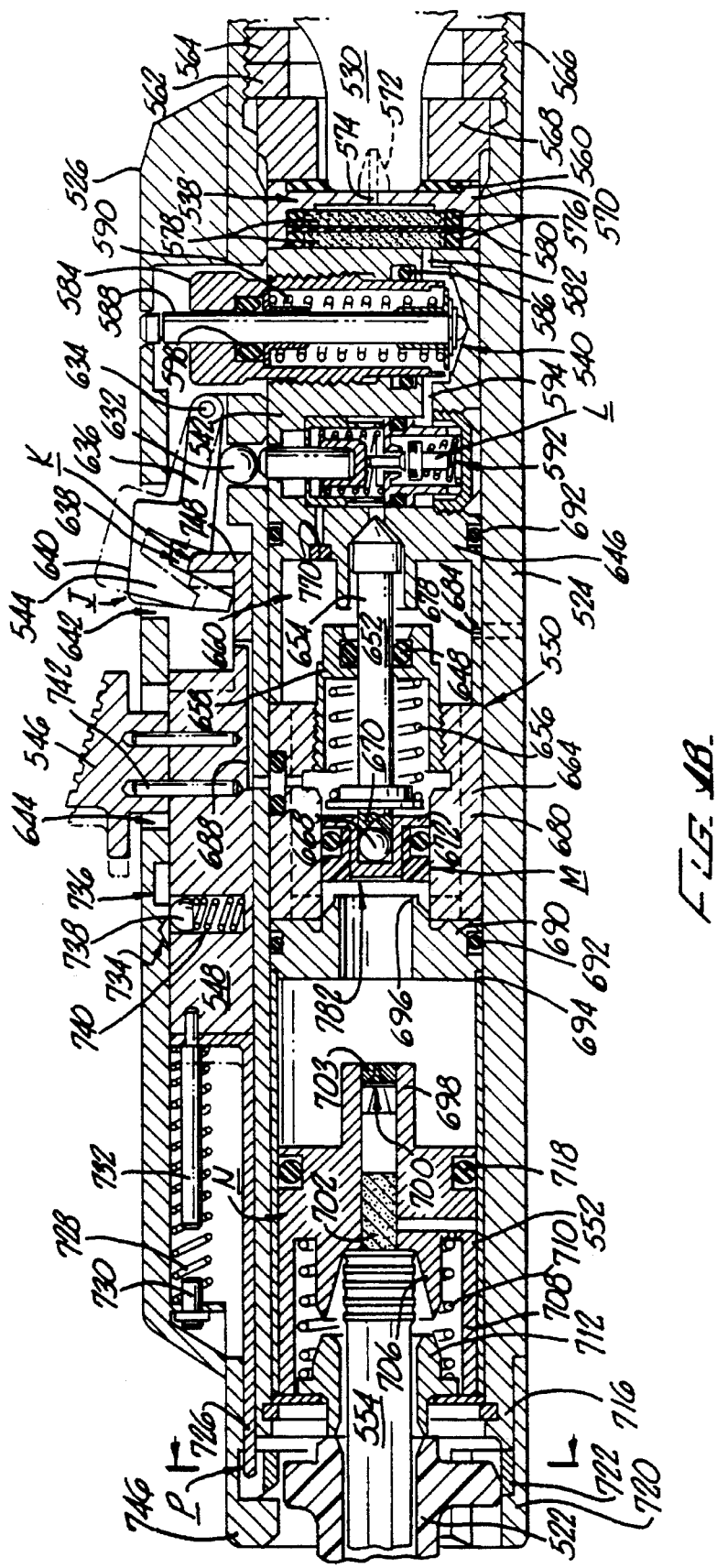
FIG. 16 is a schematically illustrated side section view of the injection device of FIG. 15.

As shown in FIG. 16, the needleless injection device 520 has a tubular housing 524 and a bridge section 526 attached to the housing 524. At the back end of the housing 524 is a cartridge holder 528 which holds a compressed $CO_2$ cartridge 54. A screw knob 532 is threaded through the cartridge holder 528 to drive the cartridge 530 into a piercing body assembly 538. A chamber port 536 extends through the back end of the cartridge holder 528 to vent the cartridge chamber 534 to atmosphere. A wavy bronze liner 600 between the cartridge 54 and cartridge holder increases heat transfer to the cartridge by improving metal-to-metal contact. Copper wool may also be pressed against the rounded back end of the cartridge 530 by a round plate on the forward end of the screw knob 532, to further increase heat transfer to the cartridge. A pressure indicator assembly 540 is contained within the housing 524 and bridge 526, in between the piercing body assembly 538 and an initiator body or valve body 542. A trigger 544 protrudes through a trigger opening 642 above the bridge 526 over the initiator body 542. A safety button 546 is attached to an interlock slide block 548 outside of the housing 524 and under the bridge section 526. A reservoir 660 is located in between the initiator body 542 and a poppet valve body 550 within the housing 524. A piston 552 slidably positioned within the housing 524 receives and drives an ampule plunger 554 which extends into and is provided with the disposable ampule 522.

As shown in FIG. 17, the housing 524 has a threaded back or tail section 566. A tensioning nut 562 and a lock nut 564 are tightened into the tail section 566 to hold the various internal components in position. The neck of the gas cartridge 54 is compressed against a washer face seal 560 by the screw knob 532. A spacer 568 surrounds the neck of the cartridge 530. The piercing body assembly 538 includes a piercing ring having a hollow point 572 protruding into the gas cartridge 54. A bore 574 extends through the piercing ring 570. Sintered filters 130 and a Tyvek filter 132 are included as previously described in the first embodiment. O-rings 576 seal the filters 130 against the piercing ring 570. Alternatively, filters 130 may be bonded or soldered to the piercing ring, for enhanced heat transfer to further minimize or prevent passage of any liquid beyond the filters.

FIG. 17 illustrates the needleless injection device 520 with the interlock system in the locked condition. FIG. 18 illustrates the same device in the triggered position as it appears during an injection sequence.

The pressure indicator assembly 540 includes an indicator housing 584 containing an indicator pin 588 which is biased downwardly by a compression spring 590. An O-ring 586 seals the indicator housing 584. The compression spring 590 is selected such that the indicator pin 588 will protrude slightly above the bridge 526 when the device has sufficient gas pressure for an injection. When the gas pressure is insufficient for an injection, the spring 590 drives the indicator pin 588 down and flush with the surface of the bridge 526, indicating to the user that the cartridge 530 needs to be replaced. A flange seal 598 seals the indicator pin 588 against the indicator housing 584.

An initiator assembly 592 includes the initiator body 542. A bore 582 extends from the front end of the piercing ring 570, below the indicator housing 584 and into a bore 594 leading into a lower initiator valve chamber 626 in the initiator body 542.

Figure 22:
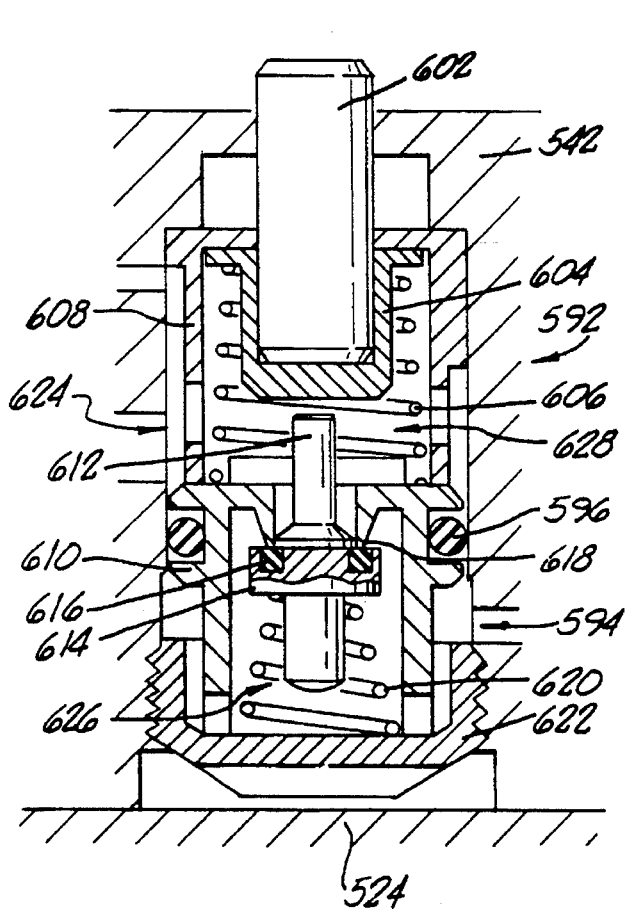
FIG. 22 is an enlarged section view fragment of the initiator valve of FIG. 15.

As shown in FIG. 22, which illustrates an enlarged detail of the initiator assembly 592 generally similar to the initiator valve 144 shown in FIG. 7, an initiator pin 602 extends above the initiator body 542 and is supported by a pin socket 604. An upper compression spring 606 biases the pin socket 604 against the upper surface of a spring guide 608. A valve stem 612 is positioned below the pin socket 604 and is upwardly biased into an initiator valve seat 610 by a lower conical compression spring 620. The valve stem 612 has a stem collar 614 having a seat ring 616 aligned with a seat neck 618 on the initiator valve seat 610. An O-ring 596 seals the initiator valve seat 610 against the initiator body 542. A hole through the stem collar 614 underneath the seat ring 616 prevents any trapped gas from dislodging the seat rung. An initiator valve nut 622 is threaded into the initiator body 542 and supports the lower compression spring 620. The lower initiator valve chamber 626 is formed by the initiator valve seat 610 and the initiator valve nut 622. The bore 594 extends into the lower chamber 626. The spring guide 608 and initiator valve seat 610 define an upper initiator valve chamber 628 connecting to a bore 624.

Referring once again to FIG. 17, a ball 632 is positioned on top of the initiator pin 602. The trigger 544 has a finger surface 640, a trigger notch 638, and a trigger arm 636 pivotally attached to the bridge 526 by a pin 634. The finger surface 640 of the trigger 544 extends through the trigger opening 642 in the bridge 526, with the device 520 in the locked position as shown in FIG. 17.

Figure 21:
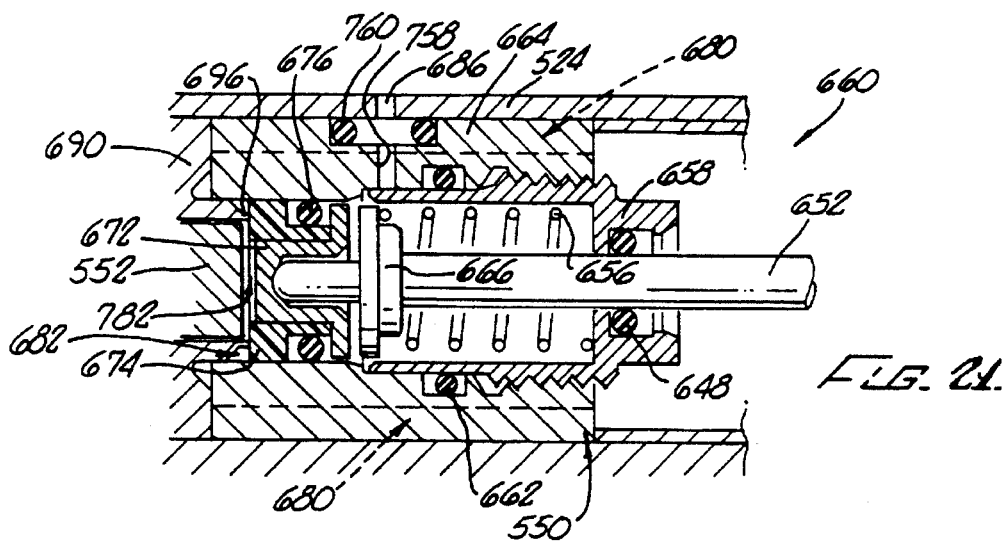
FIG. 21 is an enlarged section view fragment of an alternate embodiment of the poppet valve of FIG. 17.
Figure 23:
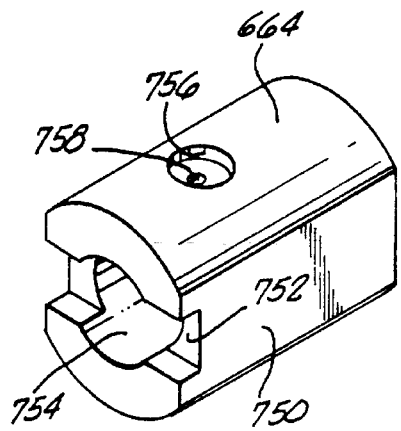
FIG. 23 is a perspective view of a poppet valve body.

Referring to FIGS. 17 and 21, a regulation valve 784 has a regulation valve body 646 sealed against the inside walls of the housing 524 by an O-ring 692. The regulation valve body 646 has a central generally conical seat 650. A valve spacer ring 786 separates the regulation valve body 646 from a poppet valve body and surrounds the reservoir 660. The wall thickness of the spacer ring 786 can be made thicker or thinner to adjust the reservoir volume and correspondingly the pressure decay profile of the injector. A poppet nut housing 658 is threaded into the back end of the poppet valve body 664 and slidably supports a poppet plunger 652 having a dart valve 654 shaped to seal against the seat 650. A compression spring 656 biases the plunger 652 forward i.e., towards the ampule 522. A spring base 666, adjacent the front end of the poppet plunger 652, supports the forward end of the poppet spring 656. As shown in FIG. 17, the forward end of the poppet plunger 652 has a ball follower 670 engaged against a float ball 668 pivotally supporting a cup 672. FIG. 21 shows an alternate embodiment wherein the cup 672 is supported on a rounded forward end of the poppet plunger 652. An annular poppet face 674 (preferably of DuPont Type 12 Nylon) is positioned over and around the cup 672 and slidably seals against a bore 754 extending through the poppet valve body 664 (FIG. 23). The ball 668 or rounded forward end of the poppet plunger 652 allows the poppet face 674 to align and orient itself within the bore 754.

A low friction seal 648 having a spring biased graphite-filled PTFE jacket (Bal. Seal Engineering Co., Inc., Santa Ana, Calif. Series 31X) seals the poppet nut housing 658 against the poppet plunger 652. The poppet nut housing 658, which is threaded into the poppet valve body 664 is also sealed against the poppet valve body 664 by an O-ring 662. Another low friction seal 676, similar to seal 648, seals the poppet face 674 and the poppet valve body 664.

Figure 24:
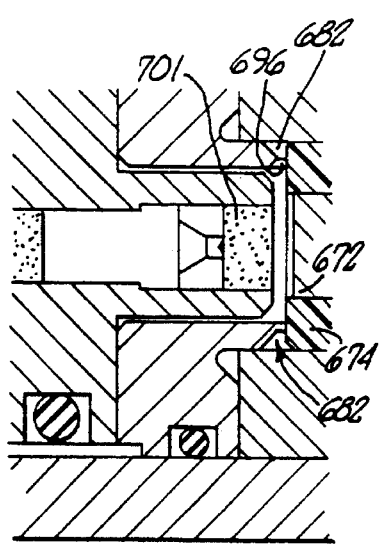
FIG. 24 is an enlarged section view fragment of the poppet plenum shown in FIG. 21.
Figure 30:
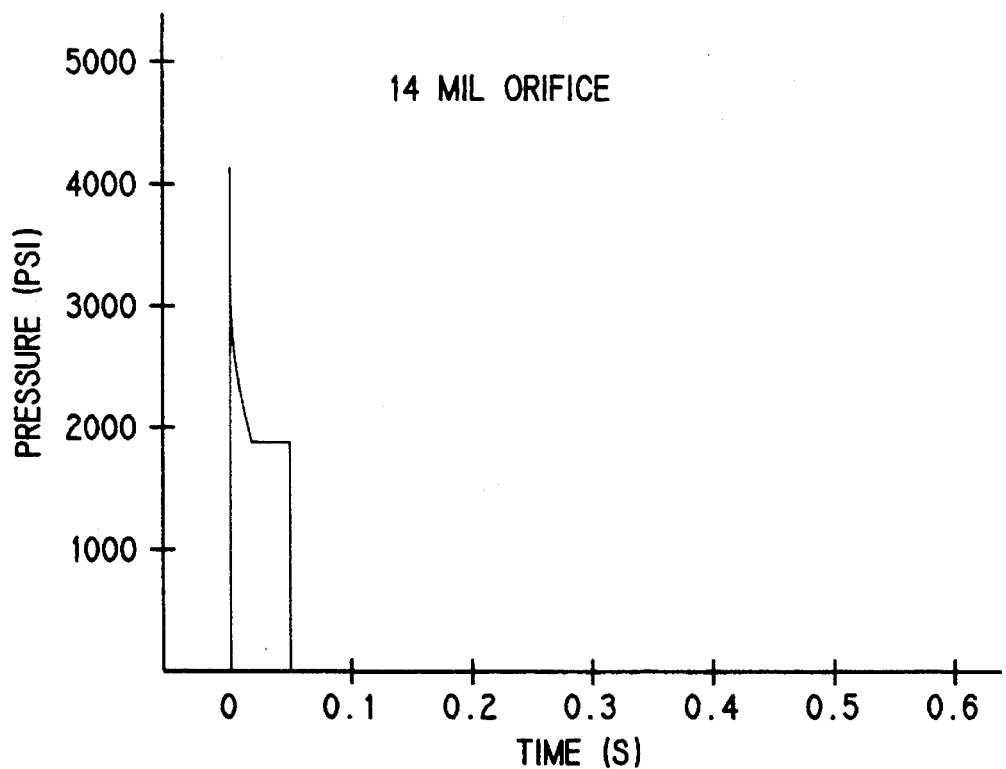
FIGS. 28, 29, and 30 are graphic illustrations of pressure-time preferred injectant pressure profiles for ampules having 0.004, 0.008 and 0.014 inch diameter nozzles, respectively.
Figure 25:
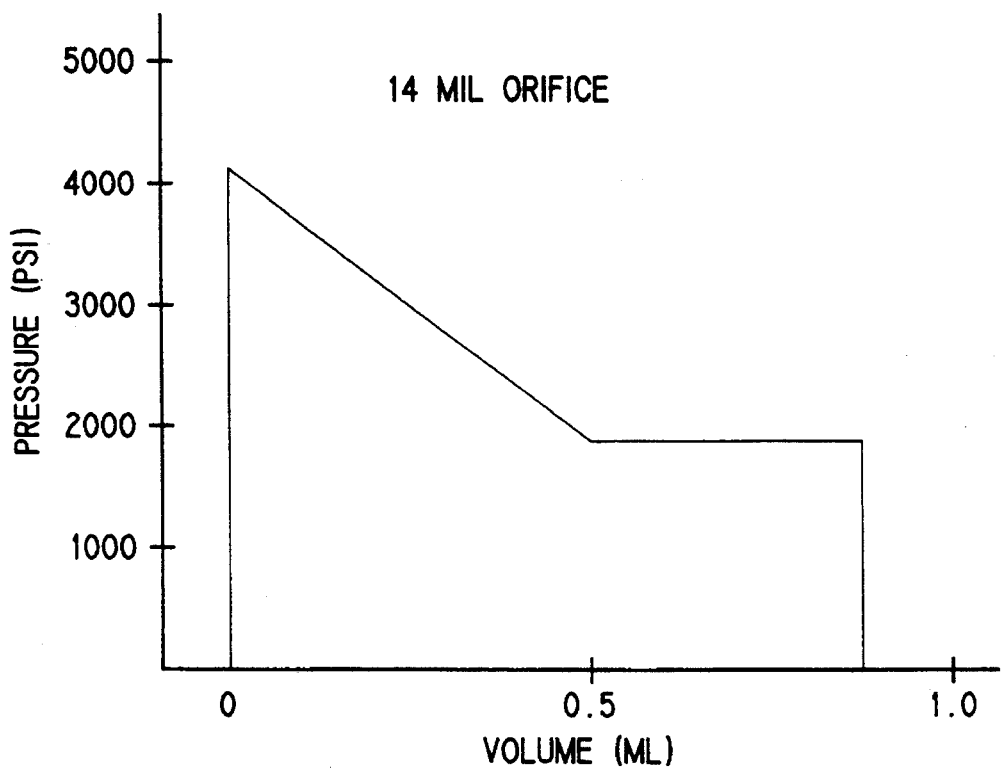
FIG. 25 is a graphic illustration of a pressure-volume preferred injectant pressure profile.
Figure 28:
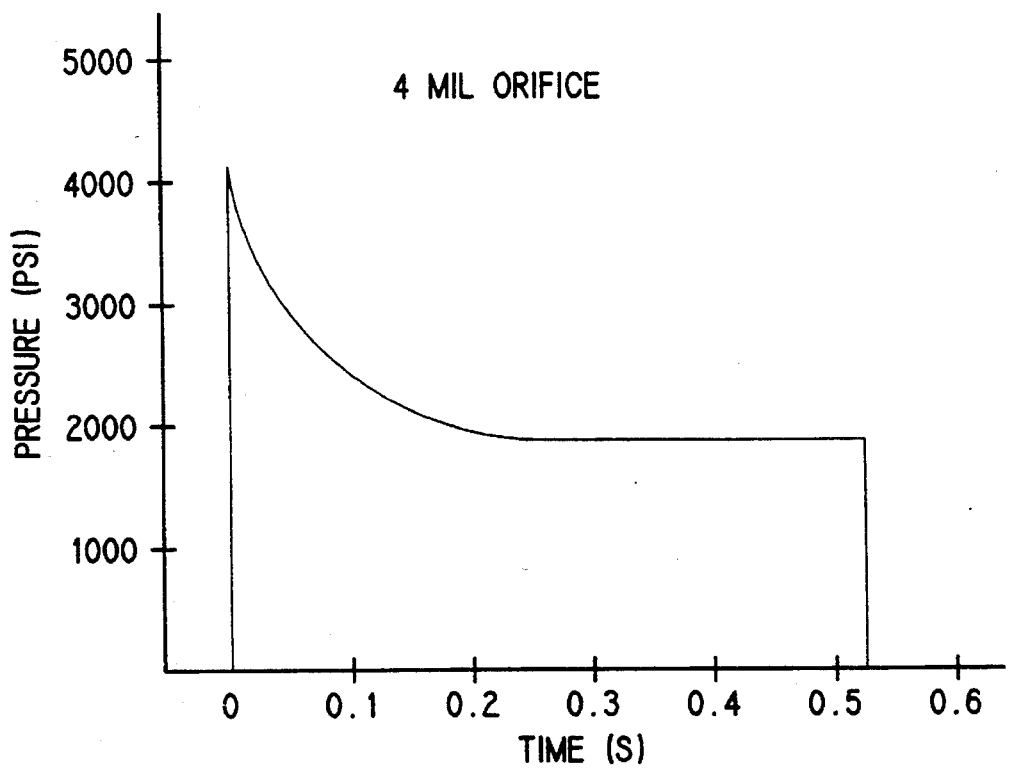
Figure 29:
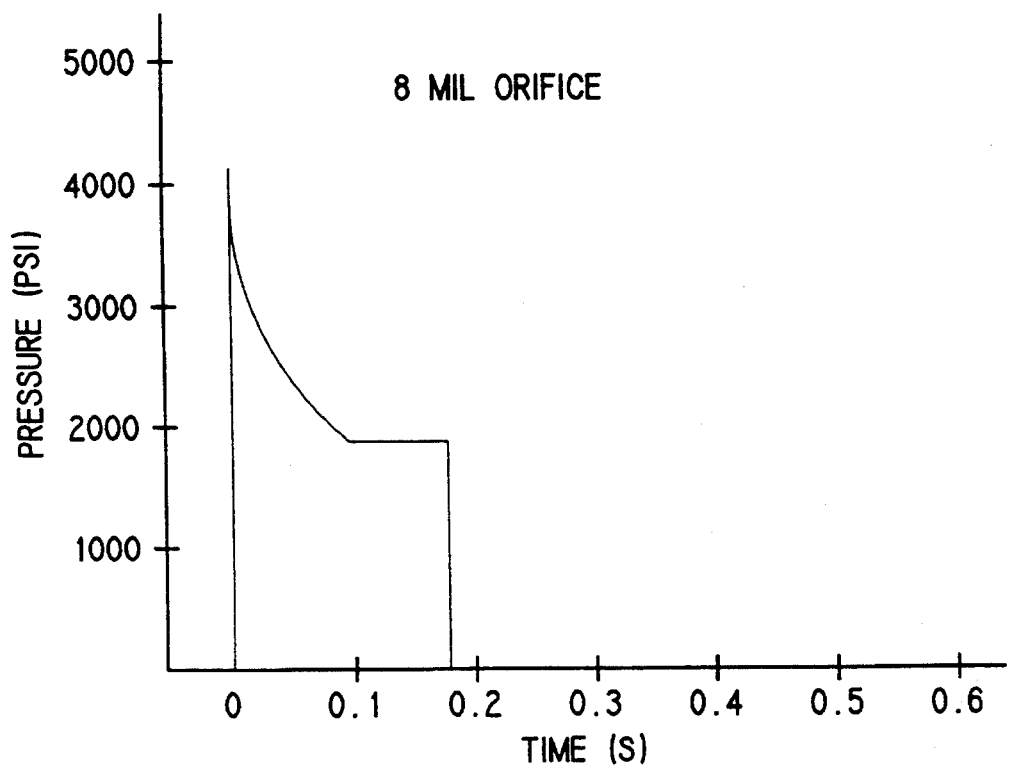

A plenum seat 690 having a rear neck ring 696 is positioned within the housing 524 against and in front of the poppet valve body 664. The neck ring 696 seals against the poppet face 674, except during actuation of the device. The piston 552 has a piston neck 698 which extends back through the plenum seat 690. Referring to FIGS. 21 and 24, the front surface of the poppet face 674, the neck ring 696 of the plenum seat 690, and the inside walls of the bore 754 in the poppet valve body, form a hollow annulus plenum 682.

With the poppet face 674 pivotably mounted to the plunger 652, the poppet face can pivot off the neck ring 696. Consistent cracking pressures (±5% peak ampule pressure variation, C.V., for all shots on a single cartridge and the same for variation between cartridges) provided by the pivoting poppet face 674 are believed to result from the pivoting or tilting separation when the valve opens. The poppet face 674 is preferably made of a low friction creep resistant material.

As shown in FIGS. 17 and 23, a double "D" shape with the poppet valve body 664 has flats 750 on its sides and a forward slot 752. Positioned within the round housing 524, the flats define reservoir feed channels 680 which connect the reservoir 660 to the poppet plenum 682, as shown in FIG. 17. A relief bore 758 and counter bore 766 extend into the top of the poppet valve body 664 to connect to a relief passage 688 in the housing 524 and bridge section 526.

A reservoir bleed bore 678 extends through the valve spacer ring 786 and the housing 524. A bleed orifice 684 is provided in the bleed bore 678 to restrict flow.

With reference to FIG. 17, the piston 552 has a piston bore 700 extending through the piston neck 698 and connecting to a drive chamber 782. The drive chamber 782 is separated and sealed from the surrounding annulus plenum 682 by the neck ring 696. The piston bore 700 leads forward from a filter 701 through an orifice 703 to a muffler 702 which in turn is joined to a release bore 704 which connects to an ampule plunger chamber 760. The filter 701 and muffler 702 are sintered stainless steel to allow for a quiet release of the gas. The ampule plunger chamber freely vents forward to ambient.

The piston 552 has an ampule plunger cup 706 with a generally conical opening to receive and secure the back end of the ampule plunger 554. The outside diameter of the ampule plunger cup 706 and a piston tube 708 extending forwardly around the ampule plunger cup 706 locate and confine a piston return spring 710. The forward end of the return spring 710 is supported by a pressure plate 712 supported by a load spreading washer 714 held in place within the housing 524 by a snap ring 716. O-ring 718 slidably seals the piston 552 against the piston sleeve 694. A front end retainer has three equally spaced apart lugs 746. The retainer 720 is bonded onto the housing 624.

Referring to FIGS. 17 and 19, an ampule indicator ring 722 is rotatably positioned within the retainer 720. The ampule indicator ring 722 has a pin slot 768 and indicator sections 724 painted with e.g., green paint. The retainer 720 has viewing ports 744 on opposite sides. A ring detent ball 762 is biased outwardly from the ampule indicator ring 722. A lock detent 764 is provided in the retainer facing the ampule indicator ring 722.

Referring to FIG. 17, an interlock spring 728 biases the slide block 548 rearwardly. The safety button 546 is attached to the interlock slide block by screws and/or pins 742. The slide block 548 has a vertical trigger stop 748 at its back end. The safety button 546 extends upwardly through a slot 644 in the bridge 526. A detent ball 738 supported by a detent spring 740 within the slide block 548 is biased into a bridge lock detent 736 on the bridge 524. A forward or actuating detent 734 is provided in the bridge 524 in front of the safety detent 736. An interlock pin 726 is attached to the slide block 548 by a spring guide rod 732 and extends forward to the ampule indicator ring 722. An interlock spring 728 supported over the spring guide rod 732 extends forward to an anchor 730 at the front end of the bridge 526.

In operation, a compressed gas cartridge, preferably a $CO_2$ cartridge 54 is placed into the cartridge holder 528. The cartridge holder 528 is then threaded into the back section of the housing 524, such that the seal in the neck of the cartridge 54 is placed against the piercing point 572 of the piercing ring 570. The screw knob 532 is turned forward to force the cartridge into the piercing point 572. The front face of the cartridge 54 seals against the washer face seal 560 while the piercing point 572 pierces open the cartridge 54.

Pressurized gas flows from the cartridge 54 through the bore 574; sintered filters 130 and Tyvek filter 132 in the piercing ring 570; through the bore 582; through the indicator chamber 558 below the pressure indicator assembly 540; through the bore 594 and into the lower chamber 626 of the initiator assembly 592. The filters substantially prevent any liquid from the cartridge 54 from passing beyond the piercing ring 570. This allows the device to be used in any orientation without effecting injection characteristics. A high heat conductivity path from the housing to the filters 578 helps to boil any liquid in the filters into gas. With sufficient gas pressure in the indicator chamber 558, the indicator pin 588 is driven upwardly and protrudes beyond the top surface of the bridge 526, thereby indicating sufficient pressure and gas volume for an injection.

A pre-filled ampule 522 with an ampule plunger 554 is placed into the front end of the device 520 by aligning the lugs at the back end of the ampule 522 to pass through the lugs 746 on the retainer 720. The detent ball 762 engaged into the detent 764 (FIG. 20) form a ring holder and provide a slight holding force on the ampule indicator ring 722 to prevent it from inadvertently rotating while the ampule is installed. With the back end of the ampule pressed against the end plate 716, the ampule 522 is rotated clockwise through an acute angle, turning the ampule indicator ring 722 from the locked position shown in FIGS. 17 and 20 to the unlocked or ready position shown in FIG. 19. The green indicator sections 724 simultaneously move into alignment with the viewing ports 744 indicating to the user that the ampule is properly positioned and the device can be enabled first and then triggered.

As shown in FIGS. 17 and 20, when the pin slot 768 in the ampule indicator ring 722 is not aligned with the interlock pin 726, the interlock slide block 548 cannot be moved forward to unlock the trigger.

Referring to FIGS. 17 and 18, with the ampule 522 properly installed in the injector 520, the pin slot 768 is aligned with the interlock pin 726. The user pushes forward on the safety button 546 which causes the interlock slide block to slide forward. While the interlock pin 726 moves forward (from position G to position P) into the pin slot 768 in the ampule indicator ring 722, the trigger lock 748 also moves forward (from position B) by an equal amount into alignment with the trigger notch 638, (to position K) as shown in FIG. 18. The detent ball 738 moves from the safety detent 736 to the actuate detent 734, to temporarily hold the slide block 548 in the forward or unlocked position against the biasing force of the interlock spring 728.

With the nozzle of the ampule 522 against the patient's skin, the trigger 630 is pressed down and pivoted (from position A in FIG. 17 to position J in FIG. 18). This causes the trigger arm 636 to push down on the ball 632. Referring to FIGS. 18 and 22, the ball 632 drives the initiator pin 602 down (from position C to position L) causing the seat ring 616 to separate from the seat neck 618, to open the initiator valve assembly 592. The compressed gas in the lower chamber 626, as well as additional compressed gas flowing from the cartridge 530, rushes through the initiator valve assembly 592 out past the seat 650 and into the reservoir 660. From there, the compressed gas flows through the reservoir feed channels 680 to the annulus plenum 682. The pressure drop across the filters 578 and 580 is low and does not significantly delay the operating time of the device.

As the gas pressure builds up in the annulus plenum 682 it eventually reaches a point when gas pressure force on the poppet face 674 equals the preset force in spring 656 and the face 674 "cracks" aways from neck ring 696. The flow of gas from the plenum 682 into drive chamber 782 also exposes the poppet face 674 and correspondingly poppet plunger 652 moves backwards very rapidly. This provides the requisite rapid pressure rise in the drive chamber 782, and also regulates the peak "cracking" pressure to negate effects of variable ambient or cartridge gas temperature. Thus the injection device 520 can achieve injections with uniform peak pressure over a wide temperature range of, for example 50°–100° F. The gas pressure in the drive chamber 782 drives the piston 552 forward causing the ampule plunger 554 to rapidly move into the ampule 522, thereby driving the injectant within the ampule 522 out of the ampule nozzle at a velocity sufficient to penetrate the patient's skin.

As the poppet plunger 652 is driven to the rear of the device 520 to operate the regulation valve 784, i.e., the dart valve 654 moves rearwardly and seals against the seat 650, thereby preventing further flow of compressed gas into the reservoir 660 and to the drive chamber 682. The gas pressure driving the piston 552 also drives the poppet plunger 652 in reverse to shut off gas flow. This allows the device to operate more independently of temperature.

A boosting channel 770 with an orifice may be provided in the regulation seat body 646 so that the dart valve 654 of the poppet plunger 652 does not entirely seal off all flow of compressed gas when it seals against the seat 650. The boosting channel 770 accordingly provides a stronger injection by decreasing the pressure decay rate during injection.

After the piston 552 is driven fully forward, as shown in FIG. 18, and the injection completed, the compressed gas remaining in the drive chamber 782 and behind the piston 552 slowly bleeds to ambient through the bleed orifice 684, piston bore 520, muffler 702, and the release bore 704. From the ampule chamber 760, the gas bleeds out through the front plate 716 and around the ampule 522. The muffler 702 reduces gas flow noises.

As the gas bleeds from the drive chamber 782, the piston return spring 710 gradually returns the piston 552 to the position shown in FIG. 17. At the same time, the poppet spring 656 returns the poppet plunger 652 to its original forward position such that the seat 650 is unsealed. The poppet face 674 moves forward and re-seals against the neck ring 696 reestablishing the annulus plenum 682 from the drive chamber 782. The reservoir 660 also bleeds to ambient through the reservoir bleed bore 678. The bleed orifice 684 through the valve spacer ring 786 and the housing 524 causes the reservoir 660 to bleed relatively slowly and silently. The spaces within the poppet body 550 also bleed through the bore 686 and relief passage 688. If there is only a small amount of pressure remaining in the gas cartridge, it is possible that even if the trigger is pressed and gas flows into the reservoir 542, the device will not operate because the gas pressure is to low to overcome the bias of spring 656 to crack the poppet face away from the neck right 696. However, if the gas remained in the reservoir, and was subsequently warmed (e.g. by a human hand) the pressure in the reservoir could increase to the cracking pressure causing the device to unintentionally actuate. The constant bleed down of the reservoir avoids this possibility.

Once the trigger 630 is released, the seat ring 616 in the initiator assembly 592 reseals against the seat neck 618 shutting off further gas flow. The safety button 546 is pushed to the back of the device 520 causing the trigger stop 748 to once again slide underneath the trigger arm 636. At the same time, the interlock pin 726 is withdrawn from the ampule indicator 722 so that the ampule 522 can be turned and removed. The device 520 is then ready for installation of another ampule and another injection.

All spaces within the device 520 from the upper chamber 628 forward are bled to ambient pressure. Accordingly, the components forward of the initiator body 542 are not pressurized in between injections, thereby reducing stresses and potential material creep distortions of non metal parts used in a lightweight and compact injector 520. The interlocking system provided by the ampule indicator ring 722 and the interlock slide block 548 prevents the injection device 520 from being fired unless an ampule is secured in proper position at the front end of the injection device 520. Since there is no rapid venting of compressed gas during injection, the injection device 520 operates relatively silently. The tubular housing 524 provides a compact linear device which facilitates handling, use, transport, and storage.

While various features and advantages are for simplicity and brevity explained and illustrated only in connection with one of the above embodiments, these features and advantages may be included in other embodiments as well, as those skilled in the art will appreciate. In addition, although several embodiments have been shown and described, it will be obvious to those skilled in the art that other variations and modifications are possible, without departing from the spirit and scope of the present invention.

We claim:

1. A device for driving a plunger into an ampule to provide a jet injection comprising:

a housing;

a driver piston slidably contained within said housing; and a clamp piston slidably positioned within said driver piston for linking said driver piston to the plunger regardless of plunger location.

2. The injection device of claim 1 further comprising a valve within said housing and means for mechanically linking said clamp piston to the plunger, controlled by the valve.

3. The device of claim 1 further comprising lugs on the ampule and said housing, for attaching the ampule to said housing.

4. The device of claim 1 further comprising clamp jaws adapted to engage a ramp drive on the clamp piston.

5. The injection device of claim 4 further comprising clamp jaw biasing means for biasing the clamp jaws apart.

6. A jet injection device, comprising:

a housing;

a driver piston contained with said housing;

an ampule releasably attached to said housing;

a plunger extending from said ampule at least partially into said housing; and a clamp piston within said driver piston for engaging onto said plunger, regardless of the position of said plunger within said housing.

7. A jet injection device comprising:

a housing;

a compressed gas source within said housing;

a driver slidably contained within said housing;

means for linking said driver to an ampule plunger, actuated by compressed gas; and a release valve within said housing for releasing compressed gas to actuate said means for linking.

8. The device of claim 7 further comprising an initiator valve for releasing compressed gas from said compressed gas source into a reservoir within the housing.

9. The device of claim 8 further comprising a regulation valve associated with said release valve, for regulating compressed gas flow into the reservoir.

* * * * *